US012594426B2

(12) United States Patent
Zhang et al.

(10) Patent No.: US 12,594,426 B2
(45) Date of Patent: Apr. 7, 2026

(54) SYSTEMS AND METHODS FOR DETECTING EVOKED COMPOUND ACTION POTENTIAL (ECAP) FEATURES IN RESPONSE TO NEUROSTIMULATION

(71) Applicant: Advanced Neuromodulation Systems, Inc., Plano, TX (US)

(72) Inventors: Mingming Zhang, McKinney, TX (US); Erika Ross, Dallas, TX (US); Yagna Pathak, Skokie, IL (US); Kyuwan Choi, Plano, TX (US); Hyun-Joo Park, Frisco, TX (US); Nishant Verma, Madison, WI (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 532 days.

(21) Appl. No.: 18/074,449

(22) Filed: Dec. 2, 2022

(65) Prior Publication Data

US 2023/0173276 A1     Jun. 8, 2023

Related U.S. Application Data

(60) Provisional application No. 63/285,723, filed on Dec. 3, 2021.

(51) Int. Cl.
| | |
|---|---|
| *A61N 1/36* | (2006.01) |
| *A61B 5/388* | (2021.01) |
(Continued)

(52) U.S. Cl.
CPC .......... *A61N 1/36139* (2013.01); *A61B 5/388* (2021.01); *A61N 1/025* (2013.01);
(Continued)

(58) Field of Classification Search
CPC .. A61N 1/36139; A61N 1/025; A61N 1/0551; A61N 1/36178; A61N 1/36192;
(Continued)

(56) References Cited

U.S. PATENT DOCUMENTS

| | | | |
|---|---|---|---|
| 4,649,482 A | 3/1987 | Raviv | |
| 10,842,997 B2 * | 11/2020 | Moffitt | .................. A61N 1/025 |
(Continued)

FOREIGN PATENT DOCUMENTS

| | | |
|---|---|---|
| WO | WO 2020223165 | 11/2020 |

OTHER PUBLICATIONS

Torrence, Christopher, and Gilbert P. Compo. "A Practical Guide to Wavelet Analysis", 1998, Bulletin of the American Meteorological Society (Year: 1998).*
(Continued)

*Primary Examiner* — Carl H Layno
*Assistant Examiner* — Mary Grace Schlueter
(74) *Attorney, Agent, or Firm* — Norton Rose Fulbright US LLP

(57) ABSTRACT

Systems and methods are disclosed for conducting spinal cord stimulation or other neurostimulation and sensing evoked compound action potential (ECAP) signals. The sensed signals may be processed to isolate ECAP features from noise and/or interfering signals. The isolated ECAP features may be used to control neurostimulation therapy for the patient and/or guide an implant procedure.

20 Claims, 33 Drawing Sheets

(51) Int. Cl.
   *A61N 1/02* (2006.01)
   *A61N 1/05* (2006.01)
   *A61N 1/372* (2006.01)
(52) U.S. Cl.
   CPC ....... *A61N 1/0551* (2013.01); *A61N 1/36178* (2013.01); *A61N 1/36192* (2013.01); *A61N 1/37223* (2013.01); *A61N 1/36062* (2017.08)
(58) Field of Classification Search
   CPC ............ A61N 1/37223; A61N 1/36062; A61N 1/0558; A61N 1/36175; A61N 1/36171; A61N 1/37241; A61N 1/37247; A61N 1/36185; A61N 1/36071; A61B 5/388; A61B 5/1116; A61B 5/389; A61B 5/4041; A61B 5/407; A61B 5/4836; A61B 5/4848; A61B 5/686; A61B 5/24; A61B 5/7257; A61B 5/726
   USPC .......................................................... 607/59
   See application file for complete search history.

(56) References Cited

U.S. PATENT DOCUMENTS

| | | | |
|---|---|---|---|
| 2004/0137515 A1 | 7/2004 | Lynch et al. | |
| 2007/0282217 A1 | 12/2007 | McGinnis | |
| 2008/0262371 A1 | 10/2008 | Causevic | |
| 2008/0300655 A1* | 12/2008 | Cholette ............ | A61N 1/36135 607/60 |
| 2010/0331916 A1 | 12/2010 | Parramon et al. | |
| 2011/0160795 A1 | 6/2011 | Osorio | |
| 2011/0184488 A1 | 7/2011 | De Ridder | |
| 2016/0051812 A1 | 2/2016 | Montgomery, Jr. | |
| 2016/0082262 A1 | 3/2016 | Parramon et al. | |
| 2016/0175594 A1 | 6/2016 | Min et al. | |
| 2016/0303376 A1 | 10/2016 | Dinsmoor et al. | |
| 2017/0259065 A1 | 9/2017 | Baru et al. | |
| 2017/0361101 A1 | 12/2017 | Single | |
| 2018/0078769 A1 | 3/2018 | Dinsmoor | |
| 2018/0117332 A1 | 5/2018 | Robinson | |
| 2018/0132760 A1 | 5/2018 | Parker | |
| 2019/0105496 A1 | 4/2019 | Min et al. | |
| 2019/0209844 A1* | 7/2019 | Esteller .............. | A61N 1/36071 |
| 2019/0366094 A1 | 12/2019 | Esteller et al. | |
| 2020/0001086 A1 | 1/2020 | Fernandez | |
| 2020/0060572 A1 | 2/2020 | Harkema | |
| 2020/0113477 A1 | 4/2020 | Dowrick et al. | |
| 2020/0282208 A1 | 9/2020 | Parker | |
| 2020/0353255 A1 | 11/2020 | Agnesi et al. | |
| 2020/0376263 A1 | 12/2020 | Zhu | |
| 2020/0391031 A1 | 12/2020 | Min et al. | |
| 2020/0402674 A1 | 12/2020 | DeBates et al. | |
| 2021/0046322 A1 | 2/2021 | Zhang et al. | |
| 2021/0236829 A1 | 8/2021 | Zhang et al. | |

OTHER PUBLICATIONS

Al-Kaisy, A. et al., "Sustained Effectiveness of 10 kHz High-Frequency Spinal Cord Stimulation for Patients with Chronic, Low Back Pain: 24-Month Results of a Prospective Multicenter Study," Pain Medicine, 2014, vol. 15, p. 347-354.

Arle, J. E. et al., "High-Frequency Stimulation of Dorsal Column Axons: Potential Underlying Mechanism of Paresthesia-Free Neuropathic Pain Relief," Neuromodulation, 2016, vol. 19, pp. 385-397.

Beurrier, C. et al., "Subthalamic Nucleus Neurons Switch from Single-Spike Activity to Burst-Firing Mode," The Journal of Neuroscience, Jan. 15, 1999, vol. 19, No. 2, pp. 599-609.

Schu, S. et al., "A Prospective, Randomised, Double-blind, Placebo-controlled Study to Examine the Effectiveness of Burst Spinal Cord Stimulation Patterns for the Treatment of Failed Back Surgery Syndrome," Neuromodulation, 2014, p. 17, pp. 443-450.

Patent Cooperation Treaty, International Search Report and Written Opinion Issued for PCT Application No. PCT/US2022/080865, dated Mar. 8, 2023, 9 pages.

Patent Cooperation Treaty, International Search Report and Written Opinion Issued for PCT Application No. PCT/US2022/080866, dated Mar. 8, 2023, 11 pages.

Patent Cooperation Treaty, International Search Report and Written Opinion Issued for PCT Application No. PCT/US2022/080868, dated Mar. 16, 2023, 9 pages.

European Search Report for European Patent Application No. 22902441.9 dated Jun. 3, 2025, 6 pgs.

Pilitsis, JG et al., The Evoked Compound Action Potential as a Predictor for Perception in Chronic Pain Patients: Tools for Automatic Spinal Cord Stimulator Programming and Control. Front. Neurosci. 15:673998. doi: 10.3389/fnins.2021.673998, (2021), 11 pages.

Lagerlund et al., Use of Principal Component Analysis in the Frequency Domain for Mapping Electroencephalographic Activities: Comparison with Phase-Encoded Fourier Spectral Analysis. Brain Topogr. 2004 Winter;17(2):73-84 (Year: 2004) , 12 pgs.

Wiest, C. et al., "Local field potential activity dynamics in response to deep brain stimulation of the subthalamic nucleus in Parkinson's disease", Neurobiology of Disease, Elsevier, Amsterdam, NL, vol. 143, Jul. 16, 2020 (Jul. 16, 2020), XP086233885, ISSN: 0969-9961, DOI: 10.1016/J.NBD.2020.105019, 15 pgs.

European Search Report for European Application No. 22902438.5 dated Sep. 9, 2025, 11 pgs.

* cited by examiner

1400

1401

Deliver pulses of a therapeutic stimulus regimen          401

Deliver one or more pinging pulses          402

Sense one or more responsive signals          403

Process sensing signals          1402

Revise one or more aspects of the therapeutic stimulation regimen          1403

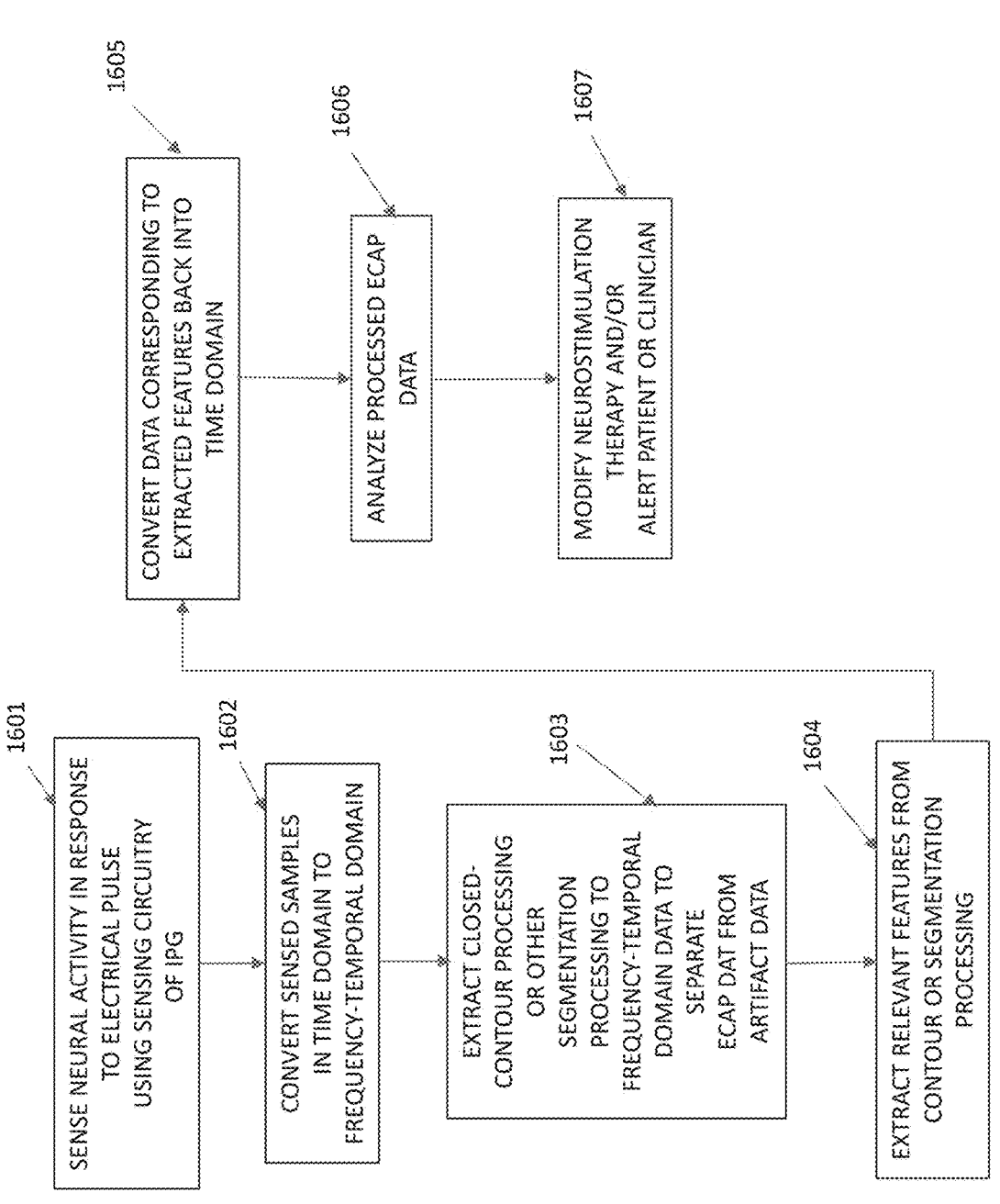

1601

SENSE NEURAL ACTIVITY IN RESPONSE TO ELECTRICAL PULSE USING SENSING CIRCUITRY OF IPG

1602

CONVERT SENSED SAMPLES IN TIME DOMAIN TO FREQUENCY-TEMPORAL DOMAIN

1603

EXTRACT CLOSED-CONTOUR PROCESSING OR OTHER SEGMENTATION PROCESSING TO FREQUENCY-TEMPORAL DOMAIN DATA TO SEPARATE ECAP DAT FROM ARTIFACT DATA

1604

EXTRACT RELEVANT FEATURES FROM CONTOUR OR SEGMENTATION PROCESSING

1605

CONVERT DATA CORRESPONDING TO EXTRACTED FEATURES BACK INTO TIME DOMAIN

1606

ANALYZE PROCESSED ECAP DATA

1607

MODIFY NEUROSTIMULATION THERAPY AND/OR ALERT PATIENT OR CLINICIAN

SYSTEMS AND METHODS FOR DETECTING EVOKED COMPOUND ACTION POTENTIAL (ECAP) FEATURES IN RESPONSE TO NEUROSTIMULATION

RELATED APPLICATION(S)

This application claims the benefit of U.S. Provisional Patent Application Ser. No. 63/285,723, filed Dec. 3, 2021, entitled "SYSTEMS AND METHODS FOR DETECTING EVOKED COMPOUND ACTION POTENTIAL (ECAP) FEATURES IN RESPONSE TO NEUROSTIMULATION," which is incorporated herein by reference in its entirety.

TECHNICAL FIELD

The present application generally relates to treating pain through electrical stimulation, and more particularly to sensing and detecting responsive signals, such as evoked compound action potentials (ECAPs), in response to the electrical stimulation.

BACKGROUND OF THE INVENTION

Implantable medical devices are used for a wide variety of medical conditions. For example, a number of implantable medical devices have been commercially distributed that allow electrical pulses or signals to be controllably delivered to targeted tissue or nerves after implantation of the respective device within a patient. Such implantable medical devices may be used for cardiac pace making, cardiac rhythm management, treatments for congestive heart failure, implanted defibrillators, and neurostimulation. Neurostimulation encompasses a wide range of applications, such as for example, treatment of chronic pain, treatment of motor disorders, treatment of incontinence and other sacral nerve related disorders, reduction of epileptic seizures, and treatment of depression. Neurostimulation in the form of spinal cord stimulation (SC S), for example, has been used as a treatment for chronic pain for a number of years. SCS is often used to alleviate pain after failed surgery, pain due to neuropathies, or pain due to inadequate blood flow. In accordance with SCS therapy, non-nociceptive fibers are stimulated to alleviate pain symptoms in cases of chronic pain.

Implantable electrical stimulation devices generally include an implanted pulse generator that generates electrical pulses or signals that are transmitted to targeted tissue or nerves through a therapy delivery element, such as a lead with an electrode array. In the case of SCS, an electrode array present on a distal end of a lead may be implanted so as to be disposed within the epidural space for delivery of the electrical stimulation. A pulse generator coupled to a proximal end of the lead may thus be enabled to apply neural stimuli to the dorsal column in order to give rise to a compound action potential (CAP). The dorsal column contains the afferent A-beta ($A\beta$) fibers to mediate sensations of touch, vibration, and pressure from the skin, whereby ones of the $A\beta$ fibers may be therapeutically recruited by the neural stimuli provided through the electrode array by the pulse generator.

According to conventional SCS, stimulation pulses are provided to neural tissue of the dorsal column in a regular pattern with each pulse having a predetermined amplitude (e.g., current intensity) and being separated by a fixed inter-pulse interval that defines a stimulation frequency configured for inducing a tingling sensation (known medically as paresthesia) in the patient. For example, stimulation of the $A\beta$ fibers may induce paresthesia and therefore may provide the mechanism of action for traditional tonic SCS to mask the pain. Although the paresthesia can be uncomfortable or even painful in patients, the paresthesia is often substantially more tolerable than the pain otherwise experienced by the patients.

A more recent approach to pain management through SCS is to use high-frequency SCS (HFSCS) to provide paresthesia-free therapy. HFSCS typically includes pulses at frequencies between 1500 Hz and 10,000 Hz although even higher frequencies could be used. In accordance with HFSCS, high-frequency electrical pulses are delivered at a current intensity below the paresthesia threshold. For example, HFSCS stimulation regimens implementing a stimulation frequency of up to 10 kHz have been found to be effective in providing pain relief without eliciting paresthesia (see e.g., Arie J E, Mei L, Carlson K W, and Shils J L, "High frequency stimulation of dorsal column axons: potential underlying mechanism of paresthesia-free neuropathic pain", Poster at International Neuromodulation Society Conference, 2015; and Adnan Al-Kaisy, MD, Jean-Pierre Van Buyten, MD, Iris Smet, MD, Stefano Palmisani, MD, David Pang, MD, and Thomas Smith, MD, "Sustained Effectiveness of 10 kHz High-Frequency Spinal Cord Stimulation for Patients with Chronic, Low Back Pain: 24-Month Results of a Prospective Multicenter Study", Pain Medicine, 2014, 15: 347-354; the disclosures of which are incorporated herein by reference.

Another approach to pain management through SCS uses a stimulation technique called burst stimulation. In implementation of burst stimulation therapy, packets (e.g., "bursts") of high-frequency impulses are delivered periodically (e.g., five pulses at 500 Hz, delivered 40 times per second) at a current intensity below the paresthesia threshold. It has been found that such burst stimulation suppresses neuropathic pain at least as well as, and possibly better than, traditional tonic SCS stimulation and provides such pain relief without eliciting paresthesia. Burst stimulation that bypasses the paresthesia process is hypothesized to have a different mechanism of action than that of traditional tonic SCS stimulation, and therefore may bypass $A\beta$ fiber activation (see e.g., Arie et al., "High frequency stimulation of dorsal column axons: potential underlying mechanism of paresthesia-free neuropathic pain", incorporated by reference above; Beurrier, et al., "Subthalamic nucleus neurons switch from single-spike activity to burst-firing mode," J. Neurosci., 19(2): 599-609, 1999; and Stefan Schu, MD, PhD, Philipp J. Slotty, MD, Gregor Bara, MD, Monika von Knop, Deborah Edgar, PhDt, Jan Vesper, MD, PhD, "A Prospective, Randomised, Double-blind, Placebo-controlled Study to Examine the Effectiveness of Burst Spinal Cord Stimulation Patterns for the Treatment of Failed Back Surgery Syndrome", Neuromodulation 2014; 17: 443-450; the disclosures of which are incorporated herein by reference.

Irrespective of the particular SCS stimulation technique implemented, stimuli amplitude (e.g., current intensity) and/or delivered charge are conventionally maintained below a comfort threshold, above which recruitment of $A\beta$ fibers may be at a level so large as to produce discomfort and even pain in the patient, in order to provide comfortable operation for a patient. Correspondingly, stimuli amplitude and/or delivered charge are generally maintained above a recruitment threshold to recruit desired action potentials for providing effective therapy to the patient (e.g., inducing an analgesic effect whereby the patient experiences no pain, or a relatively small amount of pain, at the region of interest).

Additionally, in accordance with burst stimulation techniques, stimuli amplitude and/or delivered charge are maintained below a paresthesia threshold.

Maintaining neural recruitment at an appropriate level for effectiveness of SCS and related neurostimulation therapies can be challenging due to various events, such as electrode migration and/or postural changes of the patient, that can alter the neural recruitment with respect to a particular stimulus. For example, there is room in the epidural space for an electrode array to move, whereby such movement of the electrodes may alter a distance between the electrode and one or more fibers resulting in changes to the recruitment efficacy of a particular stimulus. Additionally, the spinal cord itself may move within the cerebrospinal fluid (CSF) with respect to the dura, such as due to postural changes of the patient, whereby the distance and/or the amount of CSF between the spinal cord and the electrodes may change resulting in changes to the recruitment efficacy of a particular stimulus.

Measurement of evoked compound action potentials (ECAPs) provides a means of directly assessing the level of fiber recruitment in the dorsal columns of the spinal cord. ECAPs are signals elicited by electrical stimulations and recorded near a bundle of fibers. In particular, ECAPs usually arrive less than one millisecond (<1 ms) after a corresponding stimulation pulse and last in the range of approximately one half to one millisecond (0.5-1 ms). ECAPs may be measured and analyzed, for example, to evaluate and/or control the comfort and efficacy of a SCS treatment regimen (see e.g., US patent publication numbers 2020/0282208 A1 entitled "Neural Stimulation Dosing"; 2011/018448 A1 entitled "Spinal Cord Stimulation to Treat Pain"; and 2020/0391031 A1 entitled "System and Method to Managing Stimulation of Select A-Beta Fiber Components"; the disclosures of which are incorporated herein by reference).

BRIEF DESCRIPTION OF THE DRAWINGS

FIG. 16 depicts a flowchart for processing sensor data to isolate ECAP features for a neurostimulation therapy according to some embodiments.

FIGS. 18A-19B depict respective graphs of sensor data in the frequency-temporal domain according to some embodiments.

DETAILED DESCRIPTION OF THE INVENTION

Figure 1A:
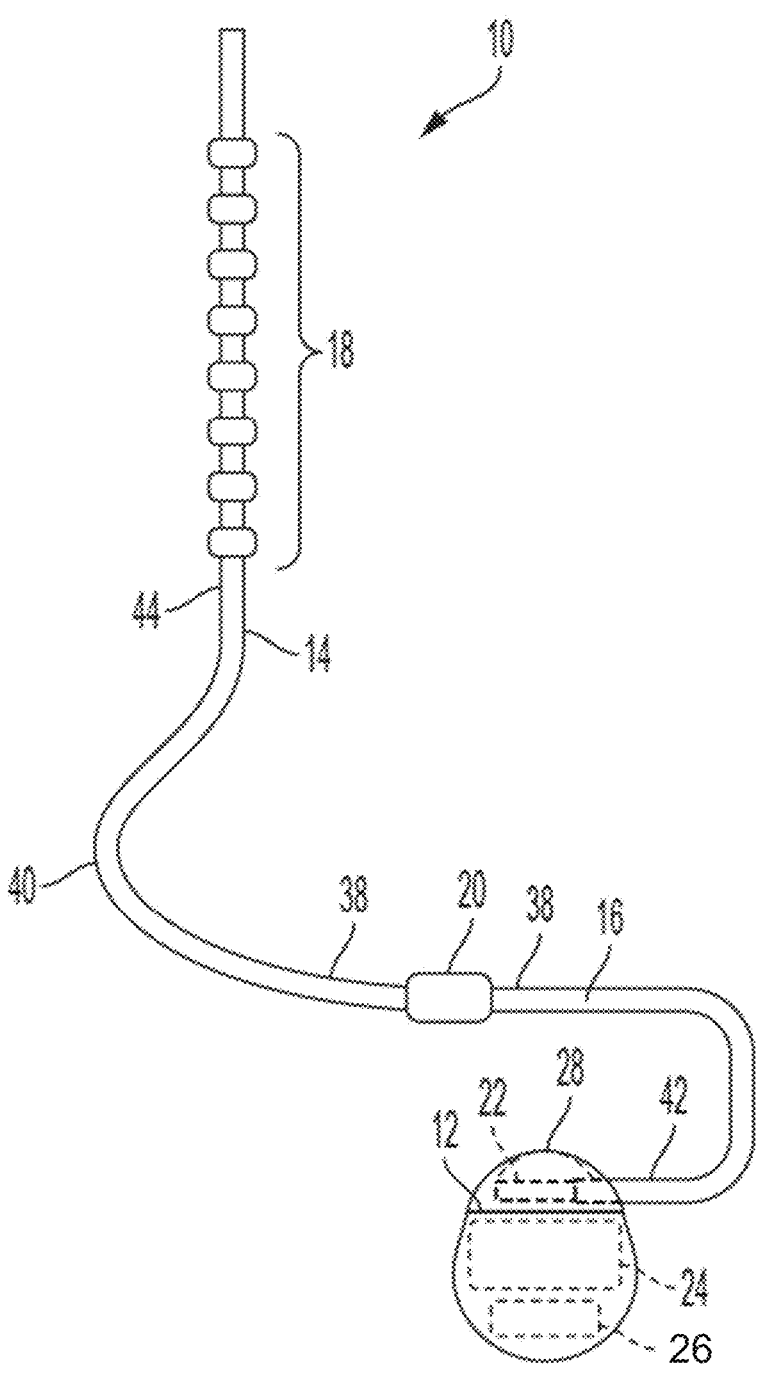
FIG. 1A shows an example stimulation system as may utilize embodiments of sensing signal stimulation of embodiments of the present invention.

Sensing signal stimulation techniques are provided according to embodiments of the invention for use in sensing responsive signals with respect to the application of paresthesia-free stimulation. For example, sensing signal initiators may be utilized with respect to implantable medical devices operable to controllably deliver electrical pulses or signals to targeted tissue or nerves after implantation of the respective device within a patient.

In the case of spinal cord stimulation (SCS), fibers that generate evoked compound action potentials (ECAPs) are generally the A-beta (Aβ) fibers located in the dorsal column. Accordingly, conventional measurement of ECAPs may be practical with respect to traditional tonic SCS, where stimulation of the Aβ fibers is performed at levels sufficient to induce paresthesia. For example, conventional ECAP sensing is known to measure the direct stimulation response to conventional tonic SCS to maintain a substantially constant level of paresthesia. However, the ECAPs for burst stimulation and high frequency stimulation may occur at sufficiently low levels that the ECAPs are not sufficient to provide an accurate assessment of the concurrent neural response. For example, burst stimulation may be provided at sufficiently low amplitudes to ensure that the patient does not experience paresthesia and thereby the resulting ECAPs do not generate an electrical field of sufficient strength for sensing using one or more electrodes of the stimulation lead. In these situations, ECAPs may not be present or may be of such low signal strength and/or present in a very low signal to noise ratio (SNR) so as to make their measurement and/or analysis impractical or even impossible.

To aid in understanding concepts herein, the description that follows describes examples relating to implantable medical devices of a spinal cord stimulation (SCS) system. However, it is to be understood that, while sensing signal stimulation techniques in accordance with concepts herein are well suited for applications in SCS, the disclosure in its broadest aspects is not so limited. Rather, sensing signal stimulation techniques of the disclosure may be used with various types of electronic stimulus delivery systems.

Sensing signal stimulation according to concepts herein may be utilized with one or more therapy delivery elements comprising an electrical lead including one or more electrodes to deliver pulses or signals to a respective target tissue site in a patient and one or more sensing electrodes to sense electrical signals at the target tissue site within the patient. In the various embodiments contemplated by this disclosure, therapy may include stimulation therapy, sensing or monitoring of one or more physiological parameters, and/or the like. A target tissue site may refer generally to the target site for implantation of a therapy delivery element, regardless of the type of therapy. The target tissue may, for example, be neural tissue of the spinal cord, dorsal root, or dorsal root ganglion in accordance with some embodiments. In accordance with some examples, one or more respective electrodes in an electrode array of an electrical lead may perform functions of both signal delivery and signal sensing.

FIG. 1A illustrates a generalized neurostimulation system (NS) 10 that may be used in SCS, as well as other stimulation applications, that generates electrical pulses for application to target tissue of the patient. NS 10 generally includes implantable pulse generator 12, implantable lead 14, which carries an array of electrodes 18 (shown exaggerated for purposes of illustration), and optional implantable extension lead 16. Although only one lead 14 is shown, often two or more leads are used with electronic stimulus delivery systems (e.g., as shown in FIG. 1C), such as for implementing a multi-stim set in which the pulse generator rapidly switches between multiple stimulation programs providing stimulation pulses to the different leads.

Lead 14 includes elongated body 40 having proximal end 36 and distal end 44. Elongated body 40 typically has a diameter of between about 0.03 inches to 0.07 inches and a length within the range of 30 cm to 90 cm for spinal cord stimulation applications. Elongated body 40 may be composed of a suitable electrically insulative material, such as a polymer (e.g., polyurethane or silicone), and may be extruded as a unibody construction.

In the illustrated embodiment, proximal end 36 of lead 14 is electrically coupled to distal end 38 of extension lead 16 via a connector 20, typically associated with the extension lead 16. Proximal end 42 of extension lead 16 is electrically coupled to implantable pulse generator 12 via connector assembly 22 associated with housing 28. Alternatively, proximal end 36 of lead 14 can be electrically coupled directly to connector 20.

In the illustrated embodiment, implantable pulse generator 12 includes electronic subassembly 24 (shown schematically), which includes control and pulse generation circuitry (not shown) for delivering electrical stimulation energy to electrodes 18 of lead 14 in a controlled manner. Implantable pulse generator 12 of the illustrated embodiment further includes a power supply, such as battery 26.

Implantable pulse generator 12 provides a programmable stimulation signal (e.g., in the form of electrical pulses or substantially continuous-time signals) that is delivered to target stimulation sites by electrodes 18. In applications with more than one lead 14, implantable pulse generator 12 may provide the same or a different signal to electrodes 18 of the therapy delivery elements.

In accordance with some embodiments, implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an inductive link. In still another embodiment, implantable pulse generator 12 can take the form of an external trial stimulator (ETS), which has similar pulse generation circuitry as an implantable pulse generator (IPG), but differs in that it is a non-implantable device that is used on a trial basis after lead 14 has been implanted and prior to implantation of the IPG, to test the responsiveness of the stimulation that is to be provided.

Housing 28 is composed of a biocompatible material, such as for example titanium, and forms a hermetically sealed compartment containing electronic subassembly 24 and battery 26 is protected from the body tissue and fluids. Connector assembly 22 is disposed in a portion of housing 28 that is, at least initially, not sealed. Connector assembly 22 carries a plurality of contacts that are electrically coupled with respective terminals at proximal ends of lead 14 or extension lead 16. Electrical conductors extend from connector assembly 22 and connect to electronic subassembly 24.

Figure 1B:
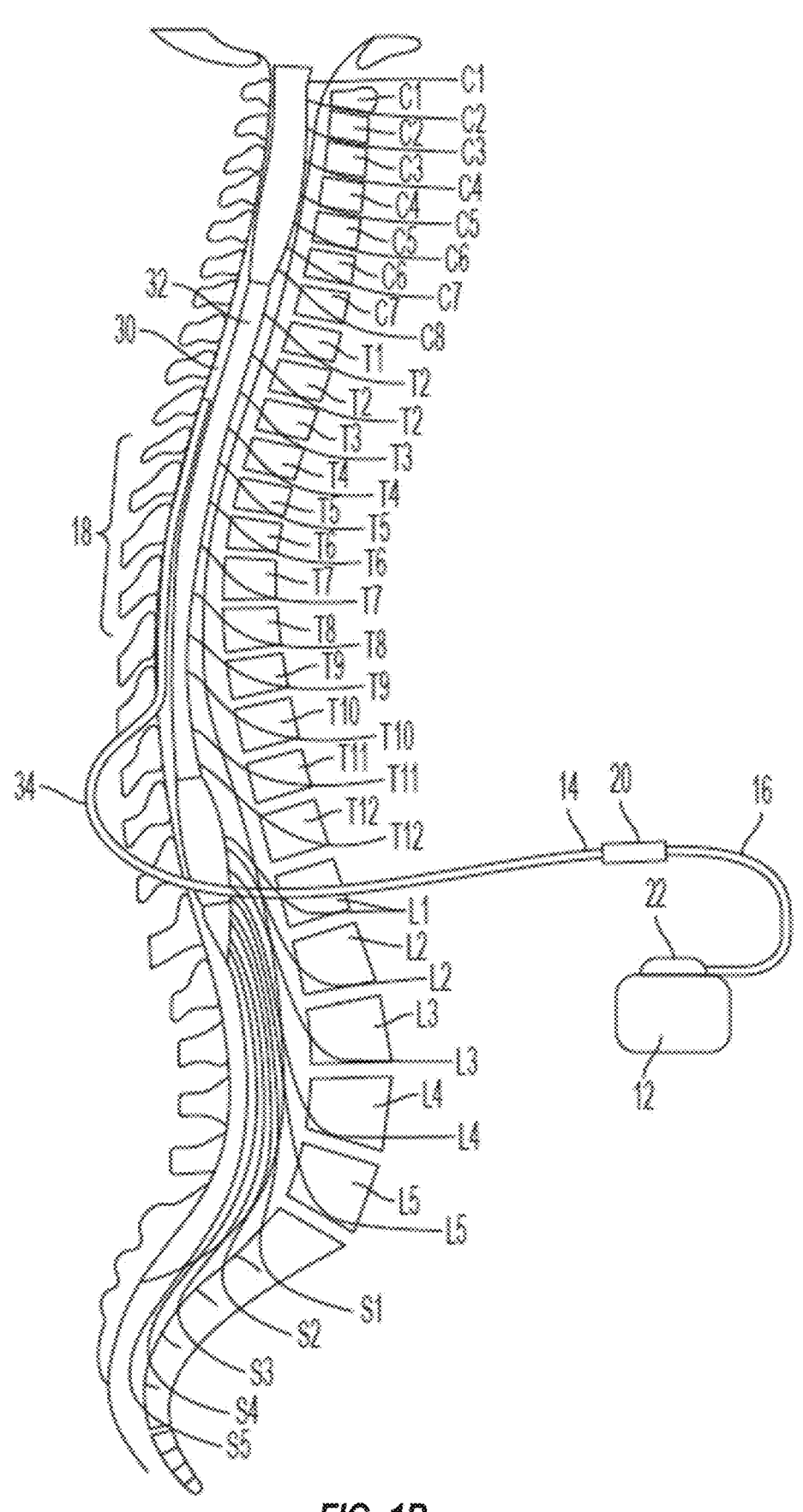
FIGS. 1B and 1C show an environment in which stimulation systems implementing sensing signal stimulation of embodiments of the present invention may be deployed.
Figure 1C:
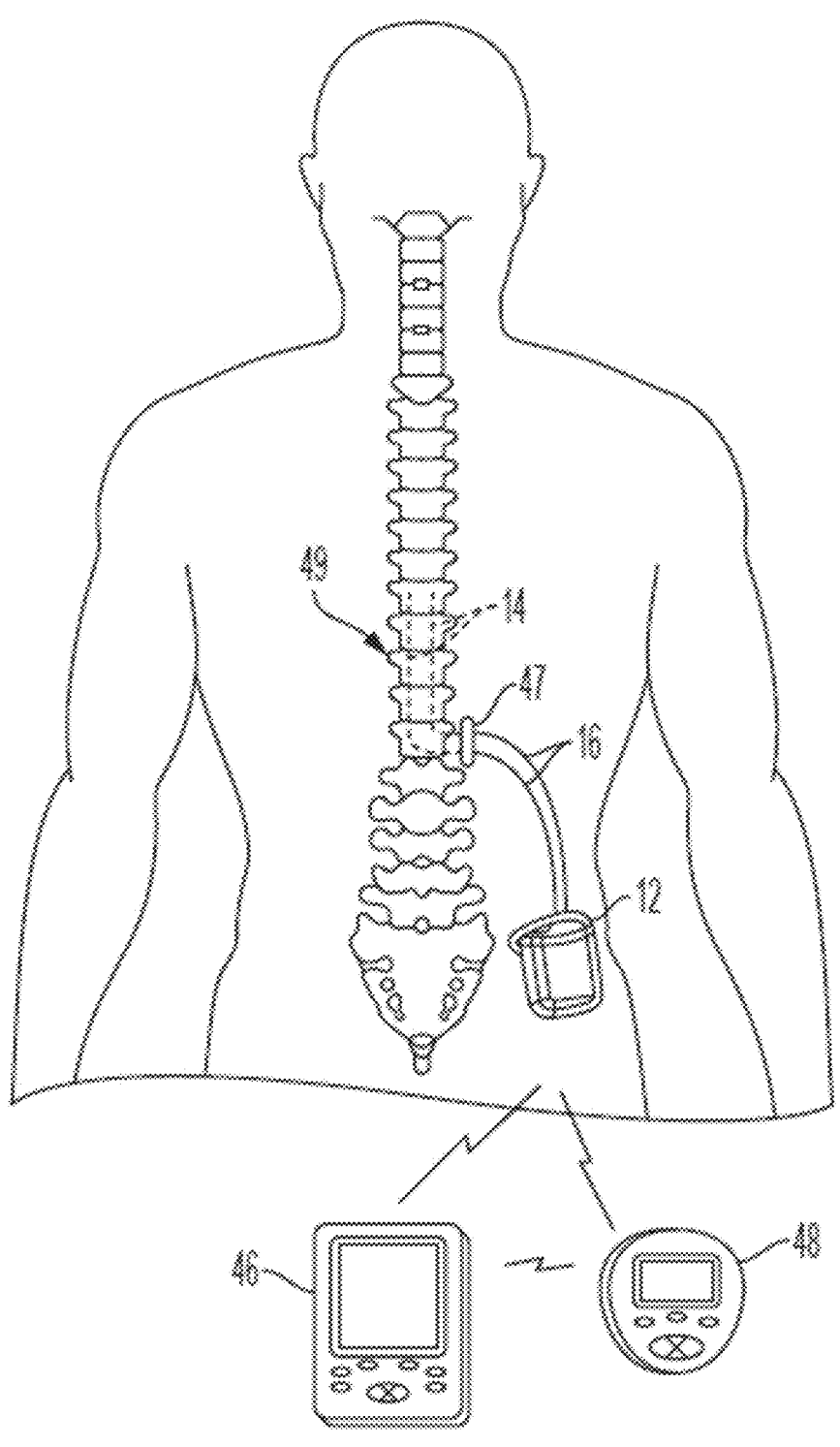

FIG. 1B illustrates lead 14 implanted in epidural space 30 of a patient in close proximity to the dura, the outer layer that surrounds spinal cord 32, to deliver the intended therapeutic effects of spinal cord electrical stimulation. The target stimulation sites may be anywhere along spinal cord 32. The target sites may, for example, include cervical, thoracic, lumbar, and sacral vertebral levels.

Because of the lack of space near lead exit point 34 where lead 14 exits the spinal column, implantable pulse generator 12 is generally implanted in a surgically-made pocket either in the abdomen or above the buttocks, such as illustrated in FIG. 1C. Implantable pulse generator 12 may, of course, also be implanted in other locations of the patient's body. Use of extension lead 16 facilitates locating implantable pulse generator 12 away from lead exit point 34. In some embodiments, extension lead 16 serves as a lead adapter if proximal end 36 of lead 14 is not compatible with connector assembly 22 of implantable pulse generator 12, since different manufacturers use different connectors at the ends of their stimulation leads and are not always compatible with connector assembly 22.

As illustrated in FIG. 1C, NS 10 also may include clinician programmer 46 and patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with implantable pulse generator 12 to download neurostimulation parameters and, optionally, upload operational or physiological data stored by implantable pulse generator 12. In this manner, the clinician may periodically interrogate implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and implantable pulse generator 12. Patient programmer 48 provides a patient with an interface for control of neurostimulation therapy provided by implantable pulse generator 12. For example, a patient may use patient programmer 48 to start, stop or adjust neurostimulation therapy. In particular, patient programmer 48 may permit a patient to adjust stimulation parameters such as duration, amplitude, pulse width and pulse rate, within an adjustment range specified by the clinician via clinician programmer 46, or select from a library of stored stimulation therapy programs.

Implantable pulse generator 12, clinician programmer 46, and patient programmer 48 may communicate via cables or a wireless communication. Clinician programmer 46 and patient programmer 48 may, for example, communicate via wireless communication with implantable pulse generator 12 using radio frequency (RF) telemetry techniques known in the art. Clinician programmer 46 and patient programmer 48 also may communicate with each other using any of a variety of local wireless communication techniques, such as RF communication according to the 802.11 or BLUETOOTH specification sets, infrared communication (e.g., according to the IrDA standard), or other standard or proprietary telemetry protocols.

Since implantable pulse generator 12 is located remotely from target location 49 for therapy, lead 14 and/or extension leads 16 is typically routed through pathways subcutaneously formed along the torso of the patient to a subcutaneous pocket where implantable pulse generator 12 is located. As used hereinafter, "lead" and "lead extension" are used interchangeably, unless content clearly dictates otherwise.

Leads are typically fixed in place near the location selected by the clinician using one or more anchors 47, such as in the epidural space 30. Anchor 47 can be positioned on lead 14 in a wide variety of locations and orientations to accommodate individual anatomical differences and the preferences of the clinician. Anchor 47 may then be affixed to tissue using fasteners, such as for example, one or more sutures, staples, screws, or other fixation devices. The tissue to which anchor 47 is affixed may include subcutaneous fascia layer, bone, or some other type of tissue. Securing anchor 47 to tissue in this manner prevents or reduces the chance that lead 14 will become dislodged or will migrate in an undesired manner.

NS 10 may be operated to controllably deliver electrical pulses or signals to targeted tissue or nerves within a patient, such as for the treatment of one or more indications. Additionally, NS 10 may be operated to sense and/or analyze signals responsive to the electronic stimuli, such as to inform fiber recruitment, to implement closed-loop feedback control of electrical pulse delivery, etc. Accordingly, electronic subassembly 24 of implantable pulse generator 12 may include processors, electronics devices, hardware devices, electronics components, logical circuits, memories, software codes, firmware codes, etc., or any combination thereof configured for controlled stimulation and/or sensing operation. One or more functional blocks of electronic subassembly 24 may, for example, be implemented as discrete gate or transistor logic, discrete hardware components, or combinations thereof configured to provide logic for performing the functions described herein. Additionally or alternatively, when implemented in software, one or more functional blocks of electronic subassembly 24, or some portion thereof, may comprise code segments (e.g., one or more instruction sets, program code, programs, applications, etc.) operable upon a processor (e.g., a processing unit having computer readable media, such as a semiconductor memory device, a read only memory (ROM), a flash memory, an erasable ROM (EROM), etc., storing instructions which when executed perform functionality described herein) to provide logic for preforming the functions described herein. Processors utilized in implementing functions herein may, for example, comprise a general-purpose processor, a digital signal processor (DSP), an application specific integrated circuit (ASIC), a field programmable gate array (FPGA), or combinations thereof.

Figure 2:
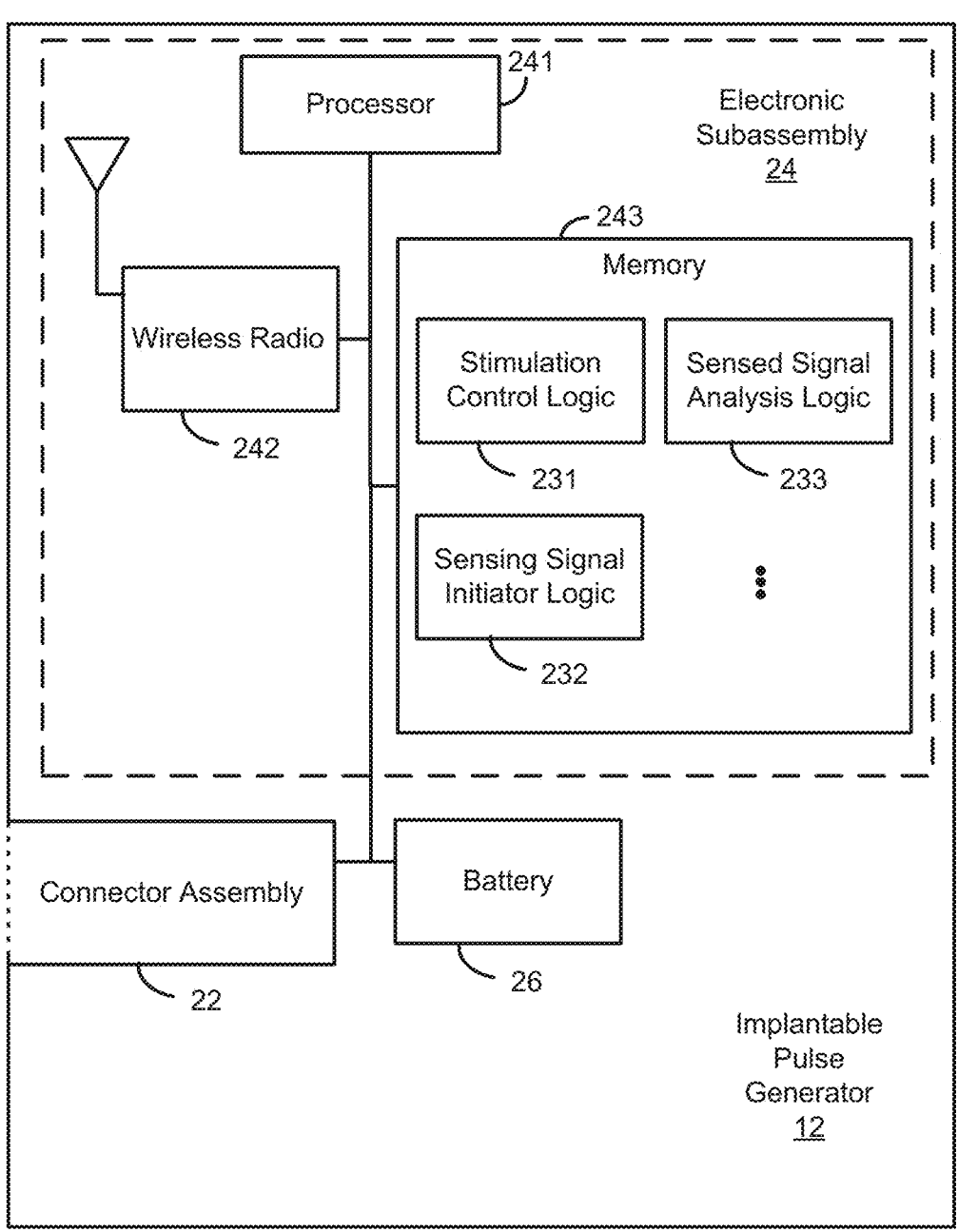
FIG. 2 shows a functional block diagram of an example implantable pulse generator adapted to elicit sensing signals according to embodiments of the present invention.

An example embodiment of implantable pulse generator 12 is illustrated in the block diagram of FIG. 2, wherein further details of exemplary electronic subassembly 24 are shown. Electronic subassembly 24 is shown in the example of FIG. 2 as being in communication with connector assembly 22 and battery 26, which may operate as described above with reference to FIGS. 1A-1C. Electronic subassembly 24 is further shown as including processor 241 in communication with wireless radio 242 and memory 243.

Wireless radio 242 may of embodiments may operate to facilitate wireless communication between implantable pulse generator 12 and one or more devices external thereto. For example, clinician programmer 46 and/or patient programmer 48 (FIG. 1C) may communicate with implantable pulse generator 12 via wireless radio 242. Wireless radio 242 may comprise an RF transceiver operable according to one or more wireless communication protocols (e.g., the 802.11 or BLUETOOTH specification sets, other standard or proprietary telemetry protocols, etc.).

Memory 243 of the example embodiment is operable to store various code segments executable by processor 241 to perform functions described herein. In particular, the code segments of the example in FIG. 2 includes stimulation control logic 231, sensing signal initiator logic 232, and sensed signal analysis logic 233. Stimulation control logic 231 may, for example, provide logic which when executed by processor 241 controls delivery of stimulation pulses to neural tissue via output of connector assembly 22 to lead 14 (FIGS. 1A-1C) according to a paresthesia-free stimulation regimen (e.g., high-frequency spinal cord stimulation (HFSCS) or burst stimulation), a conventional stimulation regimen, etc. Sensing signal initiator logic 232 of embodiments provides logic which when executed by processor 241 facilitates sensing responsive signals with respect to the application of the stimuli, such as through controlling operation to evoke responsive signals suitable for measurement and/or analysis. Sensed signal analysis logic 233 may, for example, provide logic which when executed by processor is operative to control sensing of signals, processing of sensed signals, analysis of sensed signals, and/or delivery of information (e.g., to stimulation control logic 231 executed by processor 241) regarding sensed signals. Memory 243 of embodiments may store code segments additionally or alternatively to those of the illustrated embodiment. For example, although not shown in the example of FIG. 2, memory 243 may store communication logic operable to control communication between implantable pulse generator 12 and one or more external systems (e.g., clinician programmer 46 and/or patient programmer 48), such as for receiving control signals and program code, transmitting data and telemetry, etc.

As described in further detail below, sensing signal initiator logic 232 of embodiments may operate to evoke responsive signals with sufficient signal strength and/or signal to noise (S/N) characteristics to reliably facilitate their measurement and/or analysis, even in situations where stimulation control logic 231 provides stimulation operation in accordance with a paresthesia-free stimulation regimen (e.g., HFSCS or burst stimulation). Sensed signal analysis logic 233 may thus be enabled to sense responsive signals having suitable characteristics for facilitating further processing and/or analysis, such as for informing fiber recruitment, providing information for closed-loop feedback control of the stimulus regimen by stimulation control logic 231, etc.

To aid in understanding concepts of the present invention facilitating operation as described above, examples with respect to implantable pulse generator 12 providing a burst stimulation regimen for SCS will be described. It should be appreciated, however, that concepts of the present invention may be applied with respect to various forms of paresthesia-free electrical stimulation (e.g., HFSCS, burst stimulation, high density stimulation, paresthesia-free noise stimulation, etc.) and/or for a variety of target areas (e.g., SCS, dorsal root stimulation, and dorsal root ganglion stimulation). For example, sensing signal stimulation according to some examples may be implemented with respect to a stimulation regimen which defines a high frequency stimulation pattern that is controlled with a duty cycle having on-periods and off-periods of stimulation, wherein sensing signal stimulation pinging-pulses are provided in association with off-cycles of the high frequency stimulation pattern.

Figure 3:
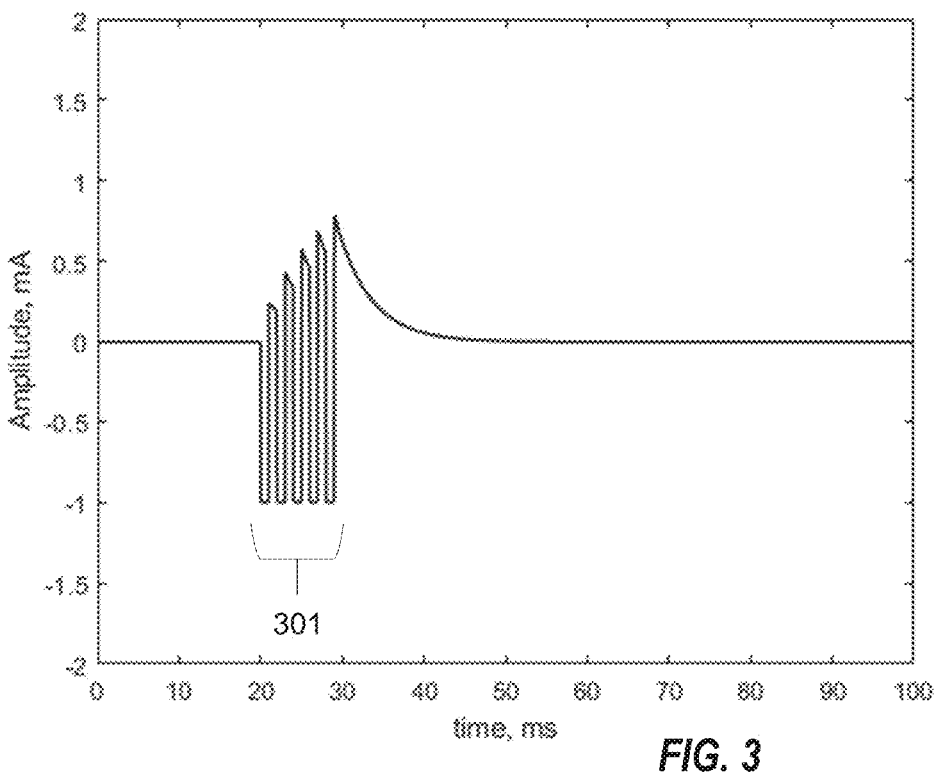
FIG. 3 shows a graph representing a burst stimulation waveform of a paresthesia-free stimulation technique.

In operation according to an exemplary embodiment, implantable pulse generator 12 may implement a burst stimulation therapy to suppresses neuropathic pain without eliciting paresthesia (e.g., paresthesia-free stimulation). In operation according to a burst stimulation regimen, packets (e.g., "bursts") of high-frequency impulses are delivered periodically at a current intensity below the paresthesia threshold. For example, a burst stimulation waveform may include five pulses of cathodic pulses (or anodic pulses at the anode) with 1000 μs pulse width each, as shown in FIG. 3 (wherein only a single burst is shown as burst 301). In a specific example, the frequency within the burst or pulse rate (the "intra-burst frequency") may be set to be 500 Hz, such as for SCS applications. Other intra-burst frequencies may be employed according to some embodiments to optimize therapy for a given patient. Continuing with the specific example, the frequency at which the bursts repeat (the "inter-burst frequency") may be nominally set to be 40 Hz, such as for SCS applications, and may be adjusted based on user preference and applications. It should be understood, however, that other intra-burst frequencies and/or inter-burst frequencies may be used, whether for SCS or other applications (e.g., the intra-burst frequency and/or nominal inter-burst frequency may be adjusted for dorsal root ganglion (DRG) stimulation).

In operation of implantable pulse generator 12, one or more signals ("responsive signals") generated or otherwise present in response to the electrical stimulation pulses may be sensed, such as for use in analyzing fiber recruitment, adjusting or otherwise controlling one or more aspect of the burst stimulation regimen, etc. An evoked neural response may, for example, be constituted of evoked compound action potentials. Evoked compound action potentials (ECAPs) are an example of responsive signals which may be sensed, processed, analyzed, and/or used in providing closed-loop feedback according to embodiments of the invention.

ECAPs are signals evoked by electrical stimulations and recorded near a bundle of fibers. ECAPs usually arrive less than 1 ms (<1 ms) after a corresponding stimulation pulse and last in the range of approximately one half to one millisecond (0.5-1 ms). In the case of SCS, the fibers that generate ECAPs are sensory fibers located in the dorsal column. With enough populational activation, sensory Aβ fibers also induce paresthesia, and therefore are the primary fibers responsible for the mechanism of action for traditional tonic SCS (e.g., generating paresthesia from Aβ fibers to mask pain). ECAPs may be measured and analyzed, for example, to evaluate and/or control the comfort and efficacy of a SCS treatment regimen. However, ECAPs or similarly generated responsive signals having signal strength, signal to noise ratio (SNR), and/or other characteristics for their reliable measurement and analysis may not be present in some situations. For example, burst stimulation at clinical amplitudes may not activate a sufficient number of dorsal column fibers, and thus usually results in no measurable or no meaningful ECAP data from sensor circuitry of the SCS IPG.

One potential solution to sensing ECAPs with respect to a paresthesia-free stimulation technique such as burst stimulation may be to increase the amplitude of the stimulation pulses of the paresthesia-free stimulation regime to beyond the level for perception and/or for generating paresthesia (e.g., burst stimulation pulses with amplitudes higher than 1.8 mA). Although this solution may be suitable in situations such as asleep implant procedures where patients do not have to experience the sensation with high stimulation pulse amplitudes, it is not well suited for general use of an implantable pulse generator to treat chronic pain of a patient. For example, the use of such increased amplitude of the pulses of otherwise paresthesia-free stimulation therapy to thereby increase the quality of the ECAP measurement and control process, would significantly reduce the patient's experience and relief of pain to the paresthesia-free stimulation therapy—essentially eliminating the paresthesia-free nature of the stimulation and likely modifying the mechanism of action.

Some embodiments of the invention utilize sensing signal initiator logic 232 in association with implementation of paresthesia-free stimulation by stimulation control logic 231 to implement sensing signal stimulation evoking responsive signals suitable for measurement and/or analysis by sensed signal analysis logic 233 without substantially changing the patient's paresthesia-free therapy into a paresthesia-based therapy. In operation according to some examples, sensing signal initiator logic 232 when executed by processor 241 may facilitate sensing of ECAPs in association with implementation of burst stimulation operating to provide paresthesia-free stimulation. Sensing signal initiator logic 232 of embodiments of the invention may, for example, control implantable pulse generator 12 to deliver one or more non-therapeutic pulses ("pinging-pulses") configured for evoking responsive signals (e.g., ECAPs) suitable for measurement and/or analysis in association with the application of neural stimuli. In operation of sensing signal initiator logic implementing sensing signal stimulation of embodiments of the invention, pinging-pulses are provided for eliciting ECAPs and/or other responsive signals with respect to paresthesia-free stimulation (e.g., burst stimulation or high frequency stimulation) substantially without eliciting paresthesia either by the pinging-pulses or the therapeutic stimulation. For example, aspects of a pinging-pulse (e.g., current intensity amplitude, pulse width, etc.) and/or pinging-pulse duty cycle (e.g., frequency of pinging-pulses, aggregate current intensity amplitude(s), aggregate pulse width(s), etc.) may be configured to avoid eliciting paresthesia in a patient.

Figure 4:
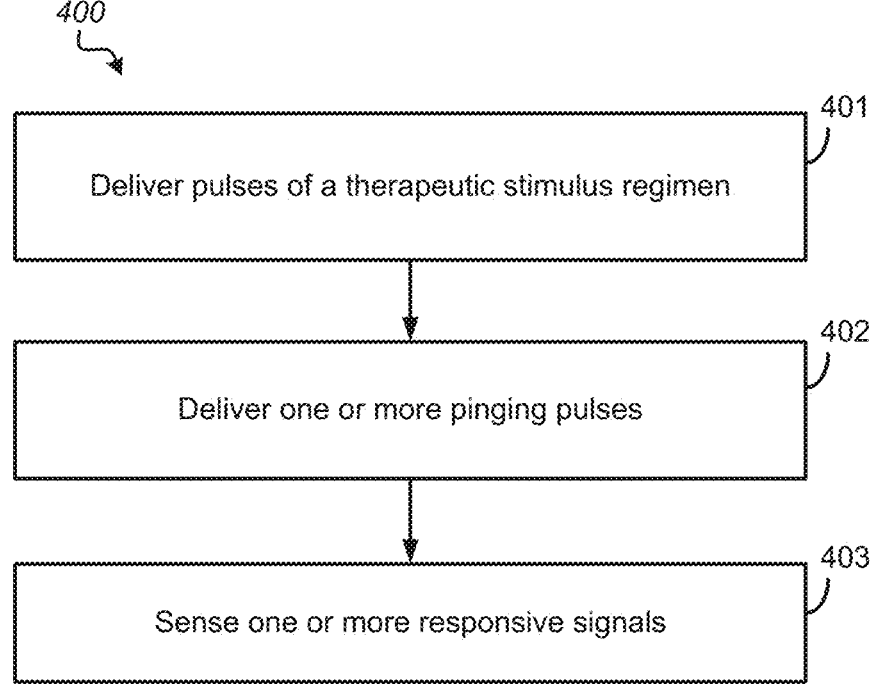
FIG. 4 shows a flow diagram of operation according to an example process to elicit sensing signals in association with corresponding therapeutic neural stimuli according to embodiments of the present invention.

FIG. 4 shows an example flow according to a process operable to evoke responsive signals suitable for measurement and/or analysis in association with the application of therapeutic neural stimuli in accordance with concepts of the present disclosure. That is, flow 400 shown in FIG. 4 provides a process to evoke sensing signals in association with corresponding therapeutic neural stimuli. The functions of flow 400 shown in FIG. 4 may, for example, be performed by an embodiment of implantable pulse generator 12, such as through operation of processor 241 executing stimulation control logic 231, sensing signal initiator logic 232, sensed signal analysis logic 233, and/or other logic for performing functions as described.

At block 401 of exemplary flow 400, pulses of a therapeutic stimulus regimen are delivered by implantable pulse generator 12, such as to target tissue within a patient via electrodes 18 of lead 14. For example, processor 241 may execute stimulation control logic 231 to provide and control delivery of the pulses of the therapeutic stimulus regimen. The amplitudes of the pulses of the therapeutic pulses of the stimulation regimen may be constant or may vary, such as according to the treatment being delivered, the particular patient being treated, etc.

The therapeutic stimulus regimen may comprise one or more a paresthesia-free stimulation regimen (e.g., high-frequency stimulation or burst stimulation), etc. In accordance with some examples, the therapeutic stimulus regimen may comprise a paresthesia-free stimulation regimen which itself results in no ECAPs or results in ECAPs of such low signal strength and/or SNR as to make their measurement and/or analysis impractical or even impossible. As a specific example, the therapeutic stimulus regimen may delivery a burst stimulation configuration of pulses, such as shown in the example of FIG. 3.

Flow 400 of the illustrated embodiment is operable to evoke responsive signals suitable for measurement and/or analysis in association with the application of the therapeutic stimulus regimen. Accordingly, at block 402, one or more pinging-pulses are delivered by implantable pulse generator 12, such as to the target tissue within the patient via electrodes 18 of lead 14. For example, processor 241 may execute sensing signal initiator logic 232 to provide and control delivery of the pinging-pulses of the sensing signal stimulation. Pinging-pulses utilized to initiate sensing signals of embodiments of the invention comprise non-therapeutic configured for evoking responsive signals suitable for measurement and/or analysis in association with the therapeutic stimulus regimen. Pinging-pulses may, for example, be provided for facilitating sensing ECAPs in association with operation of a paresthesia-free stimulation technique. According to some examples, the pinging-pulses may be provided for eliciting ECAPs with respect to burst stimulation, without eliciting paresthesia either by the pinging-pulses or the burst stimulation. In operation according to embodiments, the IPG (e.g., sensed signal analysis logic 233) may monitor a signal quality (e.g., a SNR) of the evoked neural response and control an amplitude level of the pinging-pulses in response to the quality level of the evoked neural response.

In operation at block 402 of embodiments of the invention, sensing signal initiator logic 232 may provide for an interleaved implementation to introduce the one or more pinging-pulses in between groups of pulses of the therapeutic stimulus regimen (e.g. between burst groups of a burst stimulation regimen, during a pause of appropriate duration between instances of a high frequency tonic stimulation regimen, etc.). The pinging-pulses of an interleaved implementation may, for example, comprise monophasic cathodic pulses, biphasic charge-balanced cathodic pulses (e.g., with passive or active discharge), anodic-leading actively charge-balanced pulses, or any combination thereof.

Figure 5:
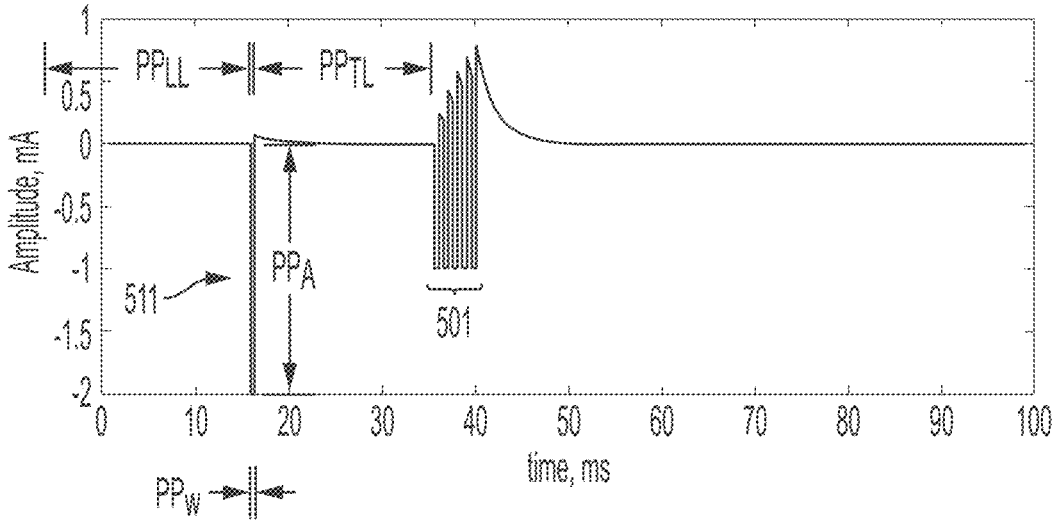
FIGS. 5-9 show graphs representing interleaved implementations of pinging-pulses delivered in association with therapeutic neural stimuli according to embodiments of the present invention.

FIG. 5 shows an example of a pinging-pulse (e.g., a cathodic pulse with passive discharge) interleaved with respect to bursts of a burst stimulation regimen. In particular, pinging-pulse 511 is shown provided within between bursts of a burst stimulation regimen (only burst 501 being shown, and it being understood that another burst having the same or different burst stimulation waveform precedes pinging-pulse 511 in the example timeline). Burst 501 may, for example, comprise a burst stimulation waveform corresponding to that of FIG. 3 described above. In operation of an interleaved pinging-pulse implementation of some examples, measuring an evoked neural response in a patient in response to the pinging-pulses occurs without including an evoked neural response to therapeutic pulses of the stimulation program Pinging-pulses of embodiments of an interleaved implementation are configured to evoke responsive signals (e.g., sensing signals) suitable for measurement and/or analysis in association with the therapeutic stimulus regimen without eliciting paresthesia. For example, various aspects of a pinging-pulse, such as one or more of pulse width, amplitude, latency between the pinging-pulse and therapeutic pulses, active discharge pulse width, anodic-leading pulse width, etc., may be selected for evoking a sensing signal without eliciting paresthesia.

According to some embodiments of an interleaved implementation of pinging-pulses, the cathodic phase of a pinging-pulse is controlled to be in the range of 60-1000 μs in pulse width (e.g., 60 μs≤$PP_W$≤1000 μs). The amplitude of the cathodic phase is selected and/or adjusted in operation according to embodiments such that a single pinging-pulse evokes one or more sensing signals (e.g., eliciting ECAPs in the dorsal column in the case of SCS). In some examples, the pinging-pulse amplitude is selected in the range of 0.5-5 mA (e.g., 0.5 mA≤$PP_A$≤5 mA). The pinging-pulse amplitude may, for example, be selected in part based upon various aspects of the particular implementation, such as pinging-pulse width, implant location, etc. A pinging-pulse trailing latency of at least 1.2 ms (e.g., $PP_{TL}$≥1.2 ms) is provided between a pinging-pulse of an interleaved implementation of embodiments and the subsequent therapeutic pulses (e.g., the pulses of burst 501), such as to facilitate sufficient time for sensing responsive signals (e.g., ECAPs). A pinging-pulse leading latency may be based upon the intra-burst frequency of the therapeutic pulses, the pinging-pulse trailing latency, and the pinging-pulse pulse width.

Pinging-pulses of embodiments of an interleaved implementation may not be present at every interval between therapeutic pulses (e.g., a pinging-pulse may not be delivered in every inter-burst-interval whereby the frequency or duty cycle of the pinging-pulses is less than the inter-burst rate of the burst stimulation pattern). In accordance with some examples, the IPG generates the pinging-pulses at a frequency or duty cycle that is selected to be sufficiently low to prevent the pinging-pulses from generating paresthesia in the patient at an amplitude level selected to evoke a neural response for measurement by the IPG. For example, some embodiments of the invention may distribute the occurrences of pinging-pulse (e.g., maintaining the inter-pinging-pulse frequency at low rate, such as 20 Hz or lower) in order to avoid or minimize resulting paresthesia. The frequency of occurrence of the pinging-pulses may be set by a clinician during a programming process to verify the pinging-pulses do not generate paresthesia in a given patient according to some embodiments.

Figure 6:
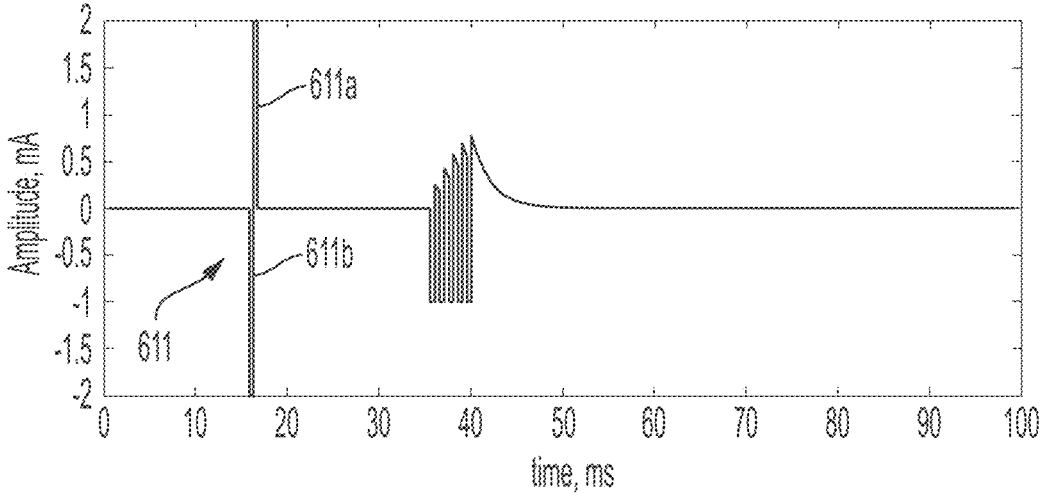

According to some embodiments of an interleaved implementation of pinging-pulses, a pinging-pulse may be provided with active discharge. FIG. 6 shows an example of a pinging-pulse with active discharge inserted between burst stimulation pulses (the preceding burst of which is not visible in the graph of FIG. 6). In the example of FIG. 6, pinging-pulse 611 includes cathodic phase 611*a* and anodic phase 611*b* (e.g., generating pairs of pulses in sequence for the pinging-pulses that have opposite polarity), wherein anodic phase 611*b* provides active discharge with respect to cathodic phase 611*a*. In operation according to embodiments in which a pinging-pulse is actively discharged, the active discharge phase (e.g., anodic phase 611*b* in the example of FIG. 6) preferably matches the pulse width of the leading phase of the pinging-pulse (e.g., cathodic phase 611*a* in the example of FIG. 6).

Figure 7:
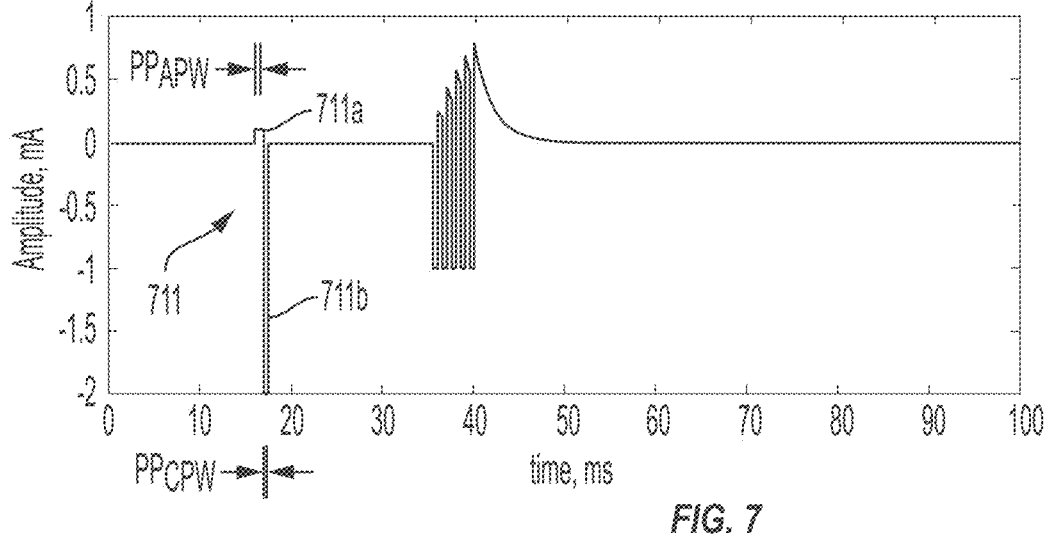

Although the foregoing examples of interleaved pinging-pulses have been with reference to pinging-pulse instances having a cathodic leading phase, it should be appreciated that pinging-pulses having an anodic leading phase may be utilized in addition to or in the alternative to pinging-pulses having a cathodic leading phase. FIG. 7 shows an example of an anodic-leading pinging-pulse with active discharge was inserted between burst stimulation pulses (the preceding burst of which is not visible in the graph of FIG. 7). In the example of FIG. 7, pinging-pulse 711 includes anodic phase 711*a* and cathodic phase 711*b*, wherein cathodic phase 711*b* provides active discharge with respect to anodic phase 711*a*. When a pinging-pulse is implemented with an anodic-leading pulse according to some embodiments of the invention, the anodic pulse width may range from 500-1000 μs (e.g., 500 μs≤$PP_{APW}$≤1000 μs), and the cathodic pulse width is preferably less than 200 μs (e.g., $PP_{CPW}$<200 μs). Such a configuration of anodic leading pinging-pulse may facilitate the cathodic phase eliciting sensing signals (e.g., responsive signals in the form of ECAPs) following the anodic phase. In operation according to embodiments of an anodic leading pinging-pulse configuration, the anodic phase provides a preconditioning pulse that increases the excitability of Aβ fibers, and the trailing cathodic pulse has higher amplitude than anodic phase pulse. The anodic and cathodic pulses can be charge balanced or slighted charge imbalanced (e.g., the charge resulting from the amplitude and pulse width of the pinging-pulse anodic phase is equal to or approximately equal to the charge resulting from the amplitude and pulse width of the pinging-pulse cathodic phase).

Figure 8:
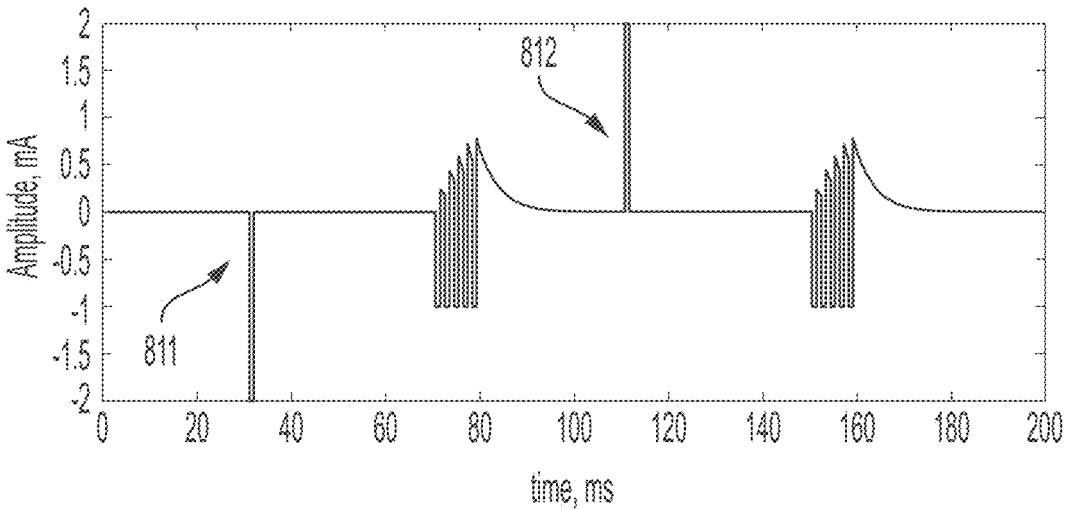

The pinging-pulses of a sequence of pinging-pulses of an interleaved implementation may each be configured the same or one or more may be configured differently. For example, interleaved pinging-pulses may be provided in an implementation in which the pinging-pulses switch between cathodal and anodal within a stimulation train. FIG. 8 shows an example of a pulse train in which pinging-pulses of alternating polarity are provided. In particular, pinging-pulse 811 of the example comprises a cathodic monophasic pulse, whereas pinging-pulse 812 comprises an anodic monophasic pulse. Such an implementation is particularly well suited for implementing monophasic pinging-pulses because the alternating pulses cancel each other. Alternating the polarity of pinging-pulses, such as shown in the example of FIG. 8, may be utilized according to embodiments of the invention to improve the SNR of elicited sensing signals. For example, the alternation in polarity may be utilized to improve the SNR of ECAPs because the opposite polarity of stim pulses can be added to zero, and the ECAPS themselves can be averaged. Such an interleaved implementation of pinging-pulses with alternating polarity allows the use of a single pulse train to improve ECAP SNR, rather than two separate pulse trains with flipped polarity of electrodes to summate to improve ECAP SNR (e.g., conducting a summation operation of the respective evoked neural response to both pulses in sequence of opposite polarity to increase signal-to-noise ratio), and therefore may reduce experimenting time by half. Additionally, the frequency of the pinging pulses may be adjusted. For example, the frequency may be controlled such that only one pinging pulses is provided between bursts for some embodiments. Lower frequency pinging pulses may be applied such that a pinging pulses are not generated before every burst but only for a subset of bursts in the overall waveform pattern. Alternatively, higher frequencies may be selected for the pinging pulses may be selected such that more than one pining pulse is provided between consecutive bursts of pulses for other embodiments.

Figure 9:
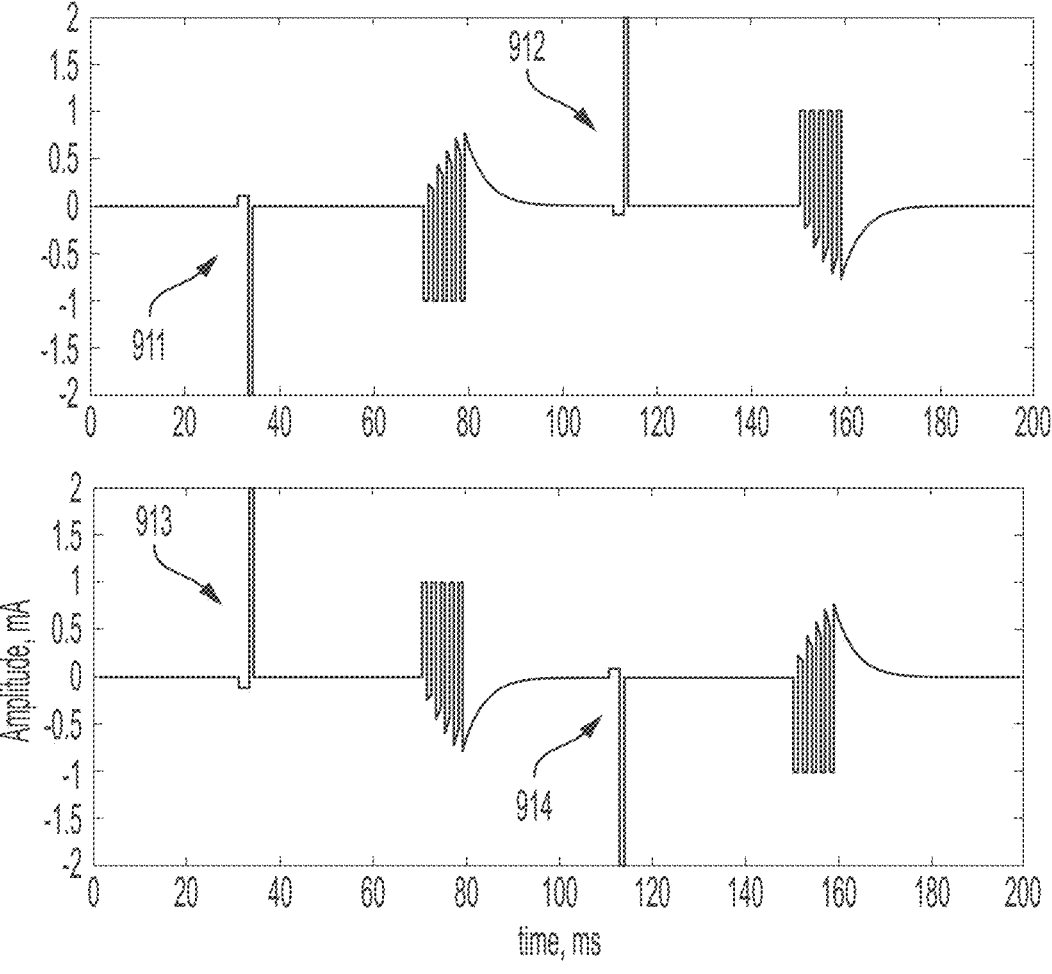

Interleaved implementations of pinging-pulses may be utilized with multi-stim sets according to embodiments of the invention. For example, interleaved pinging-pulses may be implemented via a multi-stim set in which the implantable pulse generator operates to rapidly switch between two programs of opposite polarity between electrodes. FIG. 9 shows an example of a multi-stim pulse train of two electrodes in which pinging-pulses of alternating polarities are interleaved. In particular, pinging-pulses 911 and 912 of alternating polarities in the illustrated example are interleaved in the pulse train of a first electrode and pinging-pulses 913 and 914 of alternating polarities in the example are interleaved in the pulse train of a second electrode. In addition to the pinging-pulses alternating in polarity, the therapeutic pulse groups themselves are also alternated in polarity.

In addition or in alternative to providing for an interleaved pinging-pulse implementation, operation at block 402 of embodiments of the invention may include sensing signal initiator logic 232 providing for a postfixed implementation to introduce the one or more pinging-pulses with respect to pulses of the therapeutic stimulus regimen (e.g. appended to burst groups of a burst stimulation regimen, appended to a pulse train of a high frequency tonic stimulation regimen, etc.). The pinging-pulses of a postfixed implementation may, for example, comprise pulse configurations based upon or corresponding to pulses of the therapeutic stimulus regimen.

Figure 10:
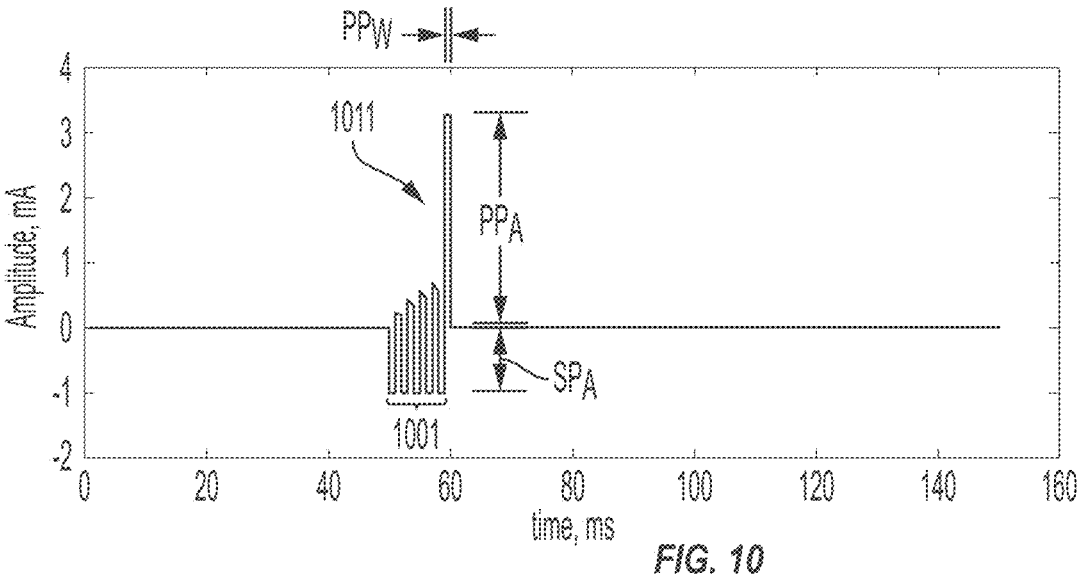
FIGS. 10-12 show graphs representing postfixed implementations of pinging-pulses delivered in association with therapeutic neural stimuli according to embodiments of the present invention.

FIG. 10 shows an example of a pinging-pulse (e.g., an anodic charge-balanced active discharge pulse) appended or postfixed to a group of therapeutic pulses. In particular, burst

1001 of a burst stimulation regimen is shown as modified to include pinging-pulse 1011 optimized for eliciting sensing signals (e.g., ECAPs). In accordance with some examples, the last passive discharge phase of a burst stimulation waveform of the burst stimulation regimen may be replaced with a pinging-pulse of embodiments of the invention. In the example of FIG. 10, an otherwise last passive discharge phase of burst 1001 has been replaced with pinging-pulse 1011 providing an active charge-balancing anodic pulse. Burst 1001 may, for example, comprise a modified burst stimulation waveform corresponding to that of FIG. 3 described above, wherein the first four bursts should have properties of the burst stimulation waveform of burst 301 and the last pulse of the burst comprises a cathodic pulse followed by an anodic pulse. Accordingly, the last passive discharge of the burst stimulation waveform of burst 301 is replaced by an active discharge in an example of burst 1001.

Pinging-pulses of embodiments of a postfixed implementation are configured to evoke responsive signals (e.g., sensing signals) suitable for measurement and/or analysis in association with the therapeutic stimulus regimen without eliciting paresthesia. For example, various aspects of a pinging-pulse, such as one or more of pulse width, amplitude, correspondence to therapeutic pulse train, etc., may be selected for invoking a sensing signal without eliciting paresthesia.

According to embodiments of a postfixed implementation of pinging-pulses, the amplitude ($PP_A$) of the anodic phase of a pinging-pulse provided with respect to a burst may be determined by calculating the total remaining charge of previous full burst groups, and dividing the charge by the pulse width of the anodic pulse. The pinging-pulse amplitude (e.g., anodic phase amplitude) of embodiments may range from 3 to 50 times the amplitude of the therapeutic stimulation pulse (e.g., cathodic phase amplitude), such as depending upon the impedance of the electrode-tissue interface and the anodic pulse width (e.g., $PP_A$ may range from 3(SPA) to 5(SPA)). In accordance with embodiments of a postfixed implementation, the pinging-pulse amplitude may be capped at the discomfort amplitude (e.g., $PP_A$<a comfort threshold) so that the patient does not feel discomfort.

Figure 11:
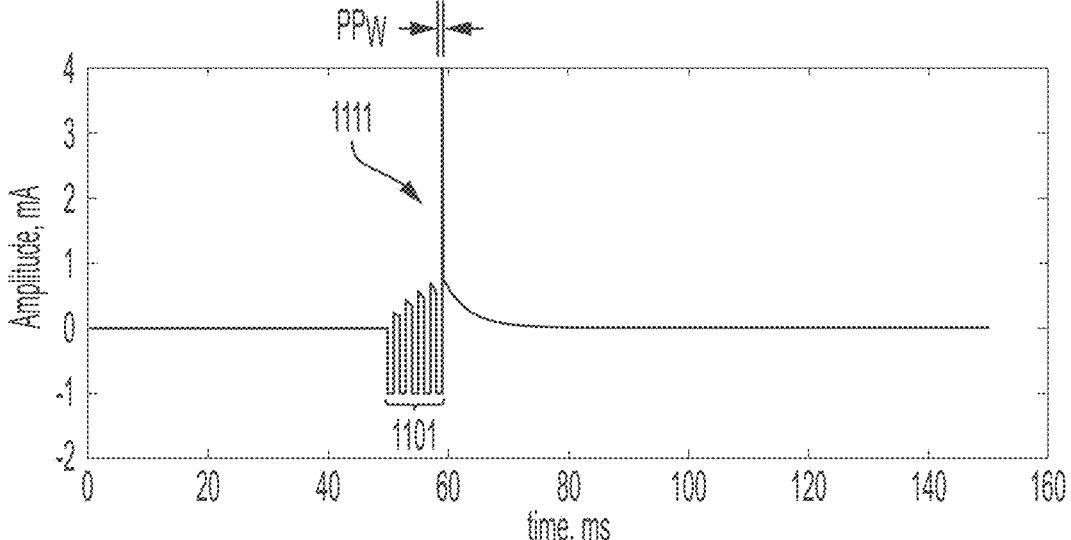

Pinging-pulses of postfixed implementations of embodiments of the invention may comprise relatively small pulse widths (e.g., 100 µs pulse width, as compared to a more common 1000 µs pulse width of a therapeutic stimulation pulse). In accordance with some embodiments, the amplitude of pinging-pulses having a small pulse width may be correspondingly capped to ensure safety. In the use of such small pulse width pinging-pulses having capped amplitudes, charge may remain that is not completely balanced. Accordingly, the implantable pulse generator may, according to some embodiments, proceed to discharge the remaining charges with passive discharge. FIG. 11 shows burst 1101 of a postfixed implementation for eliciting sensing signals (e.g., ECAPs), wherein the last passive discharge phase of the burst has been replaced with pinging-pulse 1111 comprising an active charge-balancing anodic pulse having a small pulse width. As shown in FIG. 11, the anodic pulse width of pinging-pulse 1111 is small, and the amplitude is capped, whereby passive discharge is used to discharge remaining charges. In operation according to some embodiments, a delay (e.g., trailing latency) of at least 1.2 ms (e.g., $PP_{TL} \geq 1.2$ ms) may be provided between the pinging-pulse and the passive discharge to facilitate sensing of responsive signals (e.g., ECAPs).

Figure 12:
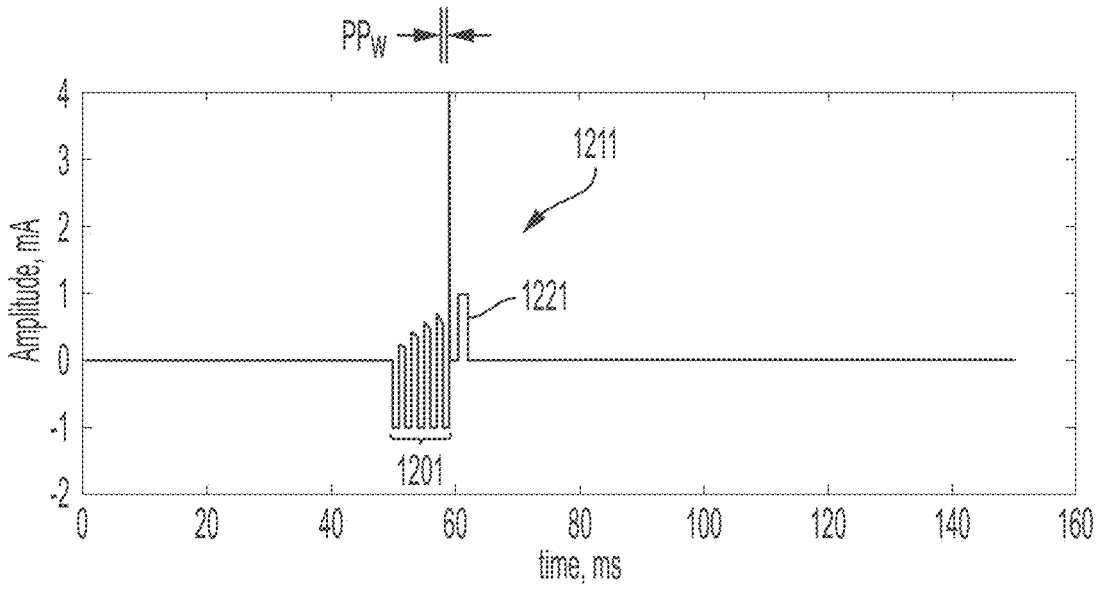

According to embodiments of a postfixed implementation of pinging-pulses, an active pulse may be provided to balance out the charges. For example, another anodic pulse of equal amplitude to that of the cathodic burst pulses may be added after the anodic pulse of a postfixed pinging-pulse. The pulse width of such as charge balancing active pulse may be calculated based on a duration to completely or substantially balance out the remaining charge. According to some examples, a trailing latency (e.g., $PP_{TL} \geq 1.2$ ms) may be provided following the pinging-pulse and before initiation of the charge balancing active pulse, such as to facilitate sensing of responsive signals (e.g., ECAPs). FIG. 12 shows burst 1201 of a postfixed implementation for eliciting sensing signals (e.g., ECAPs), wherein the last passive discharge phase of the burst has been replaced with pinging-pulse 1211 comprising an active charge-balancing anodic pulse having a small pulse width. As shown in FIG. 12, the anodic pulse width of pinging-pulse 1211 is small, and the amplitude is capped, whereby charge balancing pulse 1221 is used to implemented to balance out the charge (e.g., following a latency delay, $PP_{TL}$).

Figures 15, 17A, 17B:
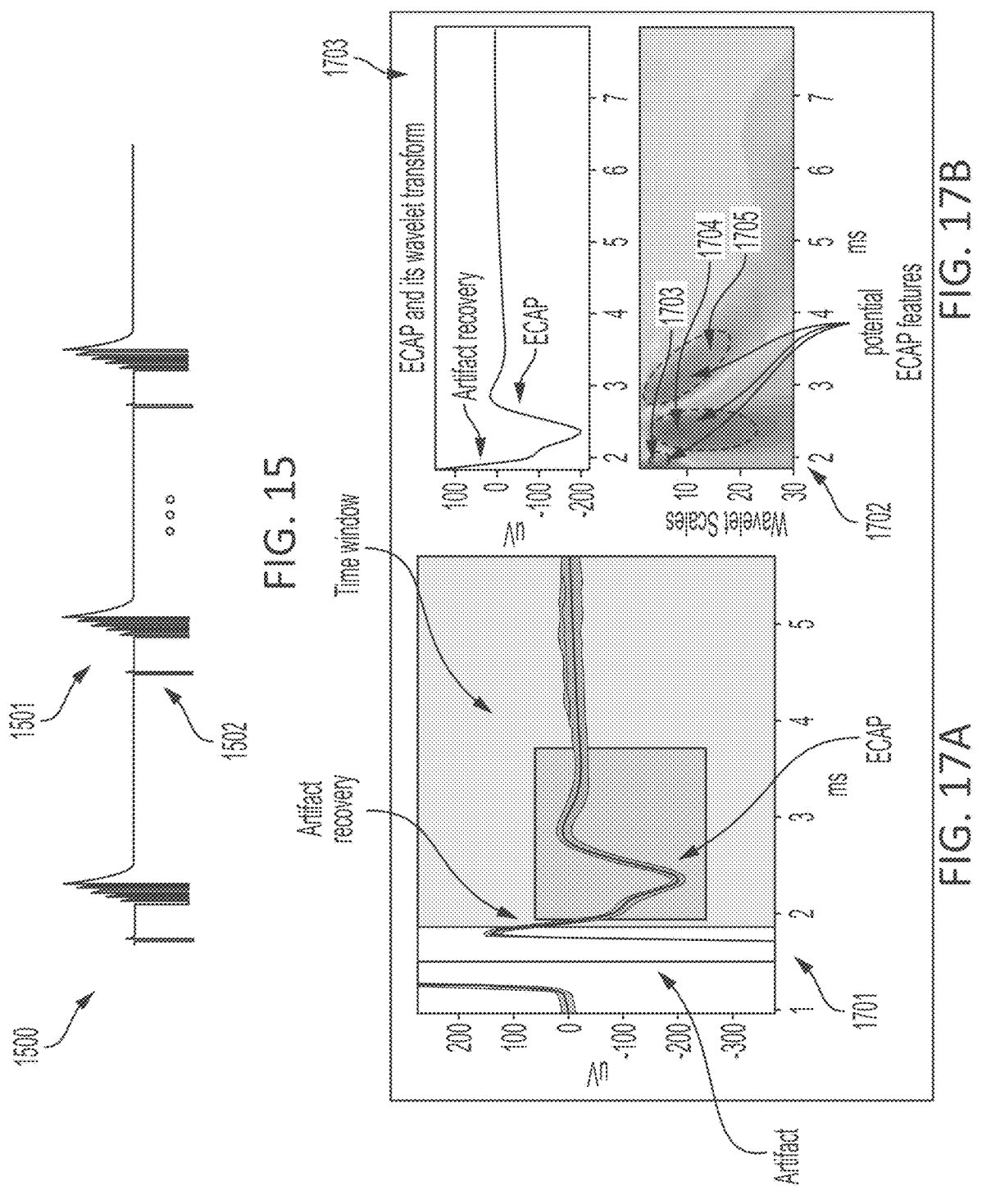
FIG. 15 depicts a graph representing interleaved implementations of pinging-pulses delivered in association with therapeutic neural stimuli according to embodiments of the present invention.
FIGS. 17A-17B depict a waveform representing sensed electrical activity corresponding to an electrical pulse and its evoked compound action potential for processing according to some embodiments.

In other embodiments, the first pulse of a burst in a stimulation pattern may be modified to promote ECAP sensing. As shown in FIG. 15, waveform pattern 1500 includes multiple bursts of pulses generated in succession including burst 1501. As shown, burst 1501 (and other burst in the pattern) includes a delay between the first pulse and the second pulse that is longer than the delay between other pulses in burst 1501. This longer delay facilitates the sensing of the ECAβ response to the first pulse of burst 1501. The delay between the first pulse and the second pulse may be a programmable setting to optimize ECAP sensing for a specific patient (either by clinician programming or automatically by sensing circuitry and ECAP signal analysis). The implementation of burst 1501 differs from the use of tonic pinging pulses in that no passive discharge occurs between the first pulse of burst 1501 and the second pulse of 1502. In some embodiments, the amplitude and/or pulse width of the first pulse may also be increased or modified to facilitate the sensing of the ECAβ response thereto.

Pinging-pulses of embodiments of a postfixed implementation may not be present with respect to every group of therapeutic pulses (e.g., a pinging-pulse may not be delivered in every inter-burst-interval). In accordance with some examples, the IPG may generate the pinging-pulses at a frequency or duty cycle that is selected to be sufficiently low to prevent the pinging-pulses from generating paresthesia in the patient at an amplitude level selected to evoke a neural response for measurement by the IPG For example, embodiments of the invention may distribute the occurrences of pinging-pulse (e.g., maintaining the inter-pinging-pulse frequency at low rate, such as 20 Hz or lower) in order to avoid or minimize resulting paresthesia. The frequency of the pinging-pulses may be set by a clinician during a programming procedure to verify that the pinging-pulses do not elicit paresthesia in a given patient.

Postfixed implementations of pinging-pulses may be utilized with multi-stim sets according to embodiments of the invention. For example, similar to the interleaved pinging-pulses implemented with respect to the multi-stim pulse train of FIG. 9 discussed above, postfixed pinging-pulses of alternating polarities may be implemented with respect to a multi-stim pulse train of two electrodes according to embodiments.

Having described examples of operation at block 402 of FIG. 4 to evoke responsive signals suitable for measurement and/or analysis in association with the application of the therapeutic stimulus regimen, and continuing with the description of flow 400, one or more responsive signals may be sensed at block 403. For example, sensing signals (e.g., ECAPs) elicited by a pinging-pulse (e.g., an instance of an interleaved pinging-pulse or a postfixed pinging-pulse) may be monitored, received, etc. by implantable pulse generator 12, such as via electrodes 18 of lead 14. In operation according to embodiments, processor 241 may execute sensed signal analysis logic 233 for monitoring sensing signals present in response to a pinging-pulse delivered by the implantable pulse generator.

Sensing signals monitored according to embodiments of the invention may be utilized in a number of ways. For example, sensed signal analysis logic 233 of embodiments may perform processing of sensing signals elicited by pinging-pulses to derive various attributes of the monitored sensing signals, such as for providing to a user (e.g., clinician), determining fiber recruitment, implementing changes to a corresponding therapeutic stimulation regimen, etc.

Figure 13:
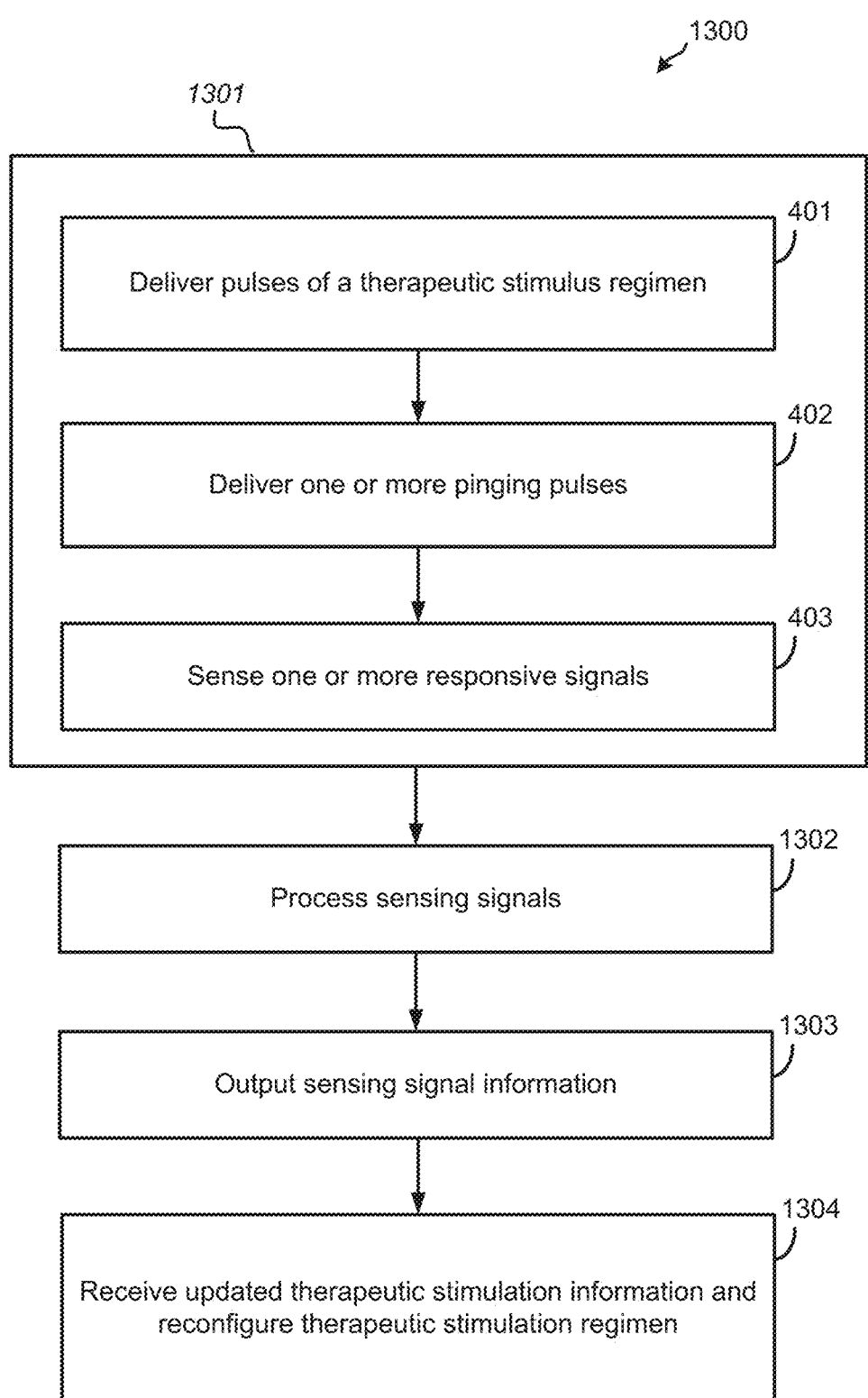
FIG. 13 shows a flow diagram of operation according to an example process in which sensing signals elicited by pinging-pulses are utilized in an open-loop implementation for configuration of a therapeutic stimulation regimen according to embodiments of the present invention.

FIG. 13 shows an example process in which sensing signals elicited by pinging-pulses of an embodiment of the invention are utilized in an open-loop implementation for configuration of a therapeutic stimulation regimen. Block 1301 of flow 1300 shown in FIG. 13 comprises a process to elicit sensing signals in association with corresponding therapeutic neural stimuli corresponding to embodiments of flow 400 described above.

As an example of operation at block 1301 of some embodiments, SCS may be provided to a patient using an IPG. The operation of this example may include selecting one or more parameters for a stimulation program for SCS to provide electrical pulses to the patient without generating paresthesia in the patient. The selecting may comprise selecting a first amplitude value to control respective pulse amplitudes of therapeutic pulses of the stimulation program. The operation may also include generating, by the IPG, electrical pulses for the stimulation program according to the one or more parameters, and generating, by the IPG, pinging-pulses at amplitudes greater than pulse amplitudes of the therapeutic pulses of the stimulation program. The pinging-pulses may be interleaved with therapeutic pulses of the stimulation program. The operation may further include applying the electrical pulses generated for the stimulation program and the pinging-pulses to neural tissue of the spinal cord without generating paresthesia in the patient, and measuring an evoked neural response in the patient in response to the pinging-pulses.

In another example of operation at block 1301 of some embodiments, SCS may be provided to a patient using an IPG. The operation of this example may include selecting one or more parameters for a stimulation program for SCS to provide electrical pulses to the patient without generating paresthesia in the patient. The operation may also include generating, by the IPG, electrical pulses for the stimulation program according to the one or more parameters. The generating electrical pulses for the stimulation program may comprise modifying a pulse amplitude of selected pulses for the stimulation program by increasing the pulse amplitude to a level for accurate measurement of a neural response by the IPG. The selected pulses may, for example, constitute twenty percent or less of a total number of pulses generated for the stimulation program. The operation may further include applying the electrical pulses generated for the stimulation program to neural tissue of the spinal cord without generating paresthesia in the patient, and measuring, by the IPG, an evoked neural response in the patient in response to pulses of stimulation program with increased pulse amplitude for accurate measurement by the IPG.

At block 1302 of the example embodiment, monitored sensing signals are processed for obtaining various information useful with respect to configuration/reconfiguration of a corresponding therapeutic stimulation regimen. For example, sensed signal analysis logic 233 of embodiments may analyze one or more sensing signals (e.g., ECAPs) to determine whether the energy content in various frequency clusters of a sensing signal is within an acceptable range (e.g., performing threshold analysis using one or more thresholds, such as a recruitment threshold, comfort threshold, paresthesia threshold, etc., representing a selected neural stimuli profile).

Correspondingly, at block 1303, sensing signal information resulting from the monitoring and processing of sensing signals may be output by the implantable pulse generator. For example, sensed signal analysis logic 233 may utilize wireless radio 242 to communicate various information with respect to one or more sensing signal, such as information indicating aspects of the effect of the stimulus regimen (e.g., that no pain or an acceptable low level of pain is experienced by the patient, that no paresthesia or an acceptably low level of paresthesia is experienced by the patient, etc.), to an external device (e.g., clinician programmer 46 of FIG. 1C).

At block 1304 of the illustrated embodiment, updated therapeutic stimulation information is received by the implantable pulse generator and the therapeutic stimulation regimen updated accordingly. For example, a clinician may refer to the sensing signal information for making one or more adjustments to neural stimuli of the therapeutic stimulation regimen, such as using clinician programmer 46. Thereafter, updated therapeutic stimulation information comprising the adjustments may be provided to stimulation control logic 231 via wireless radio 242 such that stimulation control logic 231 may reconfigure the therapeutic stimulation regimen and implement a thusly updated therapeutic stimulation regimen.

Figure 14:
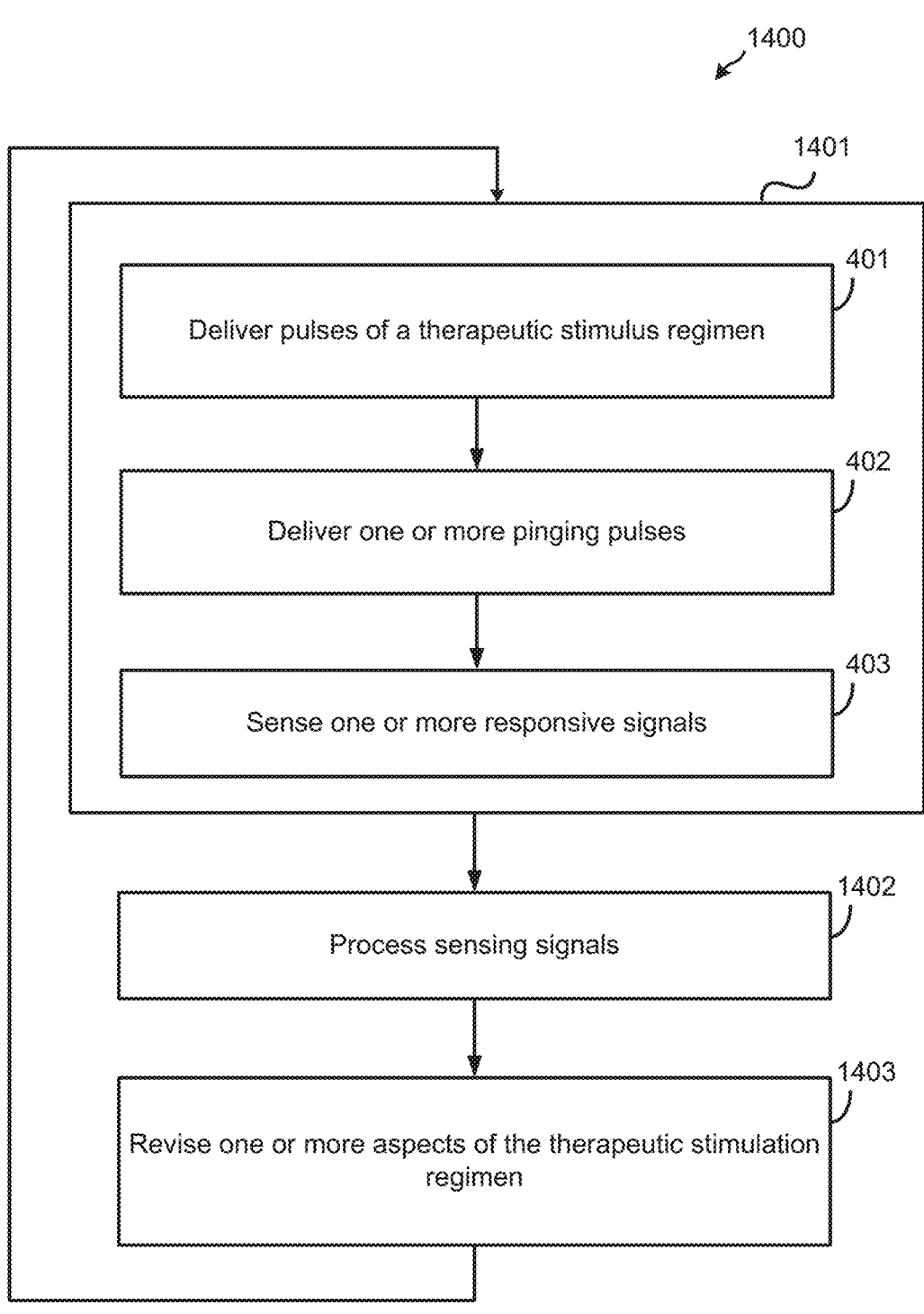
FIG. 14 shows a flow diagram of operation according to an example process in which sensing signals elicited by pinging-pulses are utilized in a closed-loop implementation for configuration of a therapeutic stimulation regimen according to embodiments of the present invention.

FIG. 14 shows an example process in which sensing signals elicited by pinging-pulses of an embodiment of the invention are utilized in a closed-loop implementation for configuration of a therapeutic stimulation regimen. Block 1401 of flow 1400 shown in FIG. 14 comprises a process to elicit sensing signals in association with corresponding therapeutic neural stimuli corresponding to embodiments of flow 400 described above.

At block 1402 of the illustrated embodiment, monitored sensing signals are processed for identifying candidate updated therapeutic stimulation waveforms. For example, sensed signal analysis logic 233 of embodiments may provide processing to convert one or more sensing signals (e.g., ECAPs) to the frequency domain (e.g., fast Fourier transform) and implement various analysis techniques, such as frequency discrimination, profile analysis, etc., to derive activity data useful in configuring/reconfiguring one or more aspect of a corresponding therapeutic stimulation regimen. In operation according to embodiments, sensed signal analysis logic 233 may analyze one or more features from a morphology of sensing signals over time, sum the occurrences of one or more features that occur with respect to sensing signals over a period of time, etc., for generating the activity data. Activity data generated through analysis of the sensing signals may be used in determining aspects of updated therapeutic stimulation waveforms.

Correspondingly, at block 1403, results of the processing and analysis of the sensing signals is utilized to revise one or more aspects of the therapeutic stimulation regimen. For example, sensed signal analysis logic 233 may provide updated therapeutic stimulation information, such as may be revised based upon activity data generated from the sensed signals, to stimulation control logic 231. Operation according to flow 1400 of some examples may thus detect a change in the evoked neural response of the patient to the pinging-pulses and automatically adjust one or more parameters for the stimulation program (e.g., modifying an amplitude level for respective pulses generated for the stimulation program without generating paresthesia in the patient) in response to detecting the change. Accordingly, stimulation control logic 231 may reconfigure the therapeutic stimulation regimen and implement the updated therapeutic stimulation regimen (e.g., returning to block 1401).

As can be appreciated from the forgoing, sensing signal stimulation implementations of embodiments of the invention evoke responsive signals with sufficient signal strength and/or S/N characteristics to provide sensing signals facilitate reliable measurement and/or analysis. Sensing signal stimulation implementations of embodiments may, for example, reliably evoke sensing signals (e.g., ECAPs) using pinging-pulses in association with paresthesia-free stimulation (e.g., burst stimulation).

In addition to modification of waveforms and/or pulse patterns to facilitate sensing of ECAPs, certain embodiments conduct other operations to facilitate ECAP sensing. These operations may be performed for the waveform/pulse patterns discussed herein and may occur for paresthesia and non-paresthesia based therapies.

ECAPs typically happen several ms after the end of the stimulation delivery. Stimulation artifact is a powerful voltage fluctuation during recording, and it takes some time to let the artifact to recover to the baseline after the stimulation ends. Often, stimulation recovery will overlap with the time window in which ECAPs signal appears, which makes the data sensing and analysis of ECAPs very difficult. Previous attempts to solve this problem use a pre-generated model to calculate the stimulation artifact recovery, and then subtract the model generated artifact recovery from the recorded signal to extract the ECAPs (Pilitsis J, et al, 2021). The disadvantage, however, is that the stimulation artifact will be different from day to day or from subject to subject, due to the movement of the recording electrodes in/on the body. Accordingly, the use of a pre-generated model to compensate for stimulation artifact in ECAP data can offer limited value.

In some embodiments, a neurostimulation system converts ECAP data in the time domain into some temporal-frequency domain signal. Then, temporal and frequency-based features are extracted to conduct signal denoising. After the feature extraction, the signal is converted back into time domain to obtain the relevant ECAP signal without noise or artifact. These processing operations are adaptive to each individual recording and there is no need to use pre-generated model. By employing processing operations in this manner, neurostimulation systems are capable of more accurately determining the effect(s) of neurostimulation and, thereby, improving patient therapy.

FIG. 16 depicts operations of a neurostimulation system for sensing and applying ECAP data according to some embodiments. In 1601, neural activity is sensed using suitable sensing circuitry of an implantable pulse generator (IPG). The sensing circuitry may include sensing circuitry described in published literature and/or used in commercial neurostimulation devices or any later developed circuitry. For ECAP applications, the sensed neural activity is neural activity that is evoked by neurostimulation. Referring to FIG. 17A, waveform 1701 represents sensed electrical activity corresponding to an electrical pulse and its evoked compound action potential. Due to the timing of the electrical pulse, recovery time, and the ECAP itself, the sensed waveform detected by the sensing circuitry may contain these various components. The sensed data may be truncated to exclude samples that include the stimulation artifact from the electrical pulse while retaining the artifact recovery component. The artifact recovery and the ECAP components in the sensed data of the truncated time window are processed as discussed herein to isolate the ECAP component for further operations of the neurostimulation system.

In 1602 of FIG. 16, the digital samples of the sensed waveform in the time domain and within a relevant time window are converted to a suitable frequency-temporal domain. In some embodiments, the processing operations to transform to a suitable frequency-temporal domain include applying the wavelet transform.

Wavelets are mathematical functions that process data into different frequency components, and then study each component with a resolution matched to its scale. Wavelet processing has advantages over traditional Fourier methods in analyzing physical situations where the signal contains discontinuities and sharp spikes. In contrast to the varieties of Fourier analysis that appropriate observed data than the sines and cosines functions, wavelet analysis employs approximating functions that are contained neatly in finite domains. The windowed Fourier transform (WFT) is a known application of representing the nonperiodic signal in a frequency-temporal domain. With the WFT, the input signal f(t) (in this case the sensed data samples containing the stimulation artifact, the artifact recovery, and the ECAP) is segmented or divided into sections or time windows, and each section/time window is analyzed for its frequency content separately. If the signal has sharp transitions, the input data may be windowed so that the sections converge to zero at the endpoints. This windowing is accomplished via a weight function that places less emphasis near the interval's endpoints than in the middle. The effect of the window is to localize the signal in time.

The processing operations of transforming signal into frequency-temporal domain are not limited to wavelet transform but may also include methods for transforming signal into frequency or scales-like signal. Such methods might include Short Time Fourier Transform (STFT/DTFT), wavelet transform, Hilbert Transform, et al. according to other embodiments.

The processing of the time domain data into the frequency-temporal domain generates a two-dimensional array of data. The two dimensions are frequency and time. Each value in the two-dimensional array represents the signal power/amplitude at a given frequency at a given time. Graph 1702 represents a graph of the two-dimensional sensed data in the frequency-temporal domain according to some embodiments.

Figures 18A, 18B:
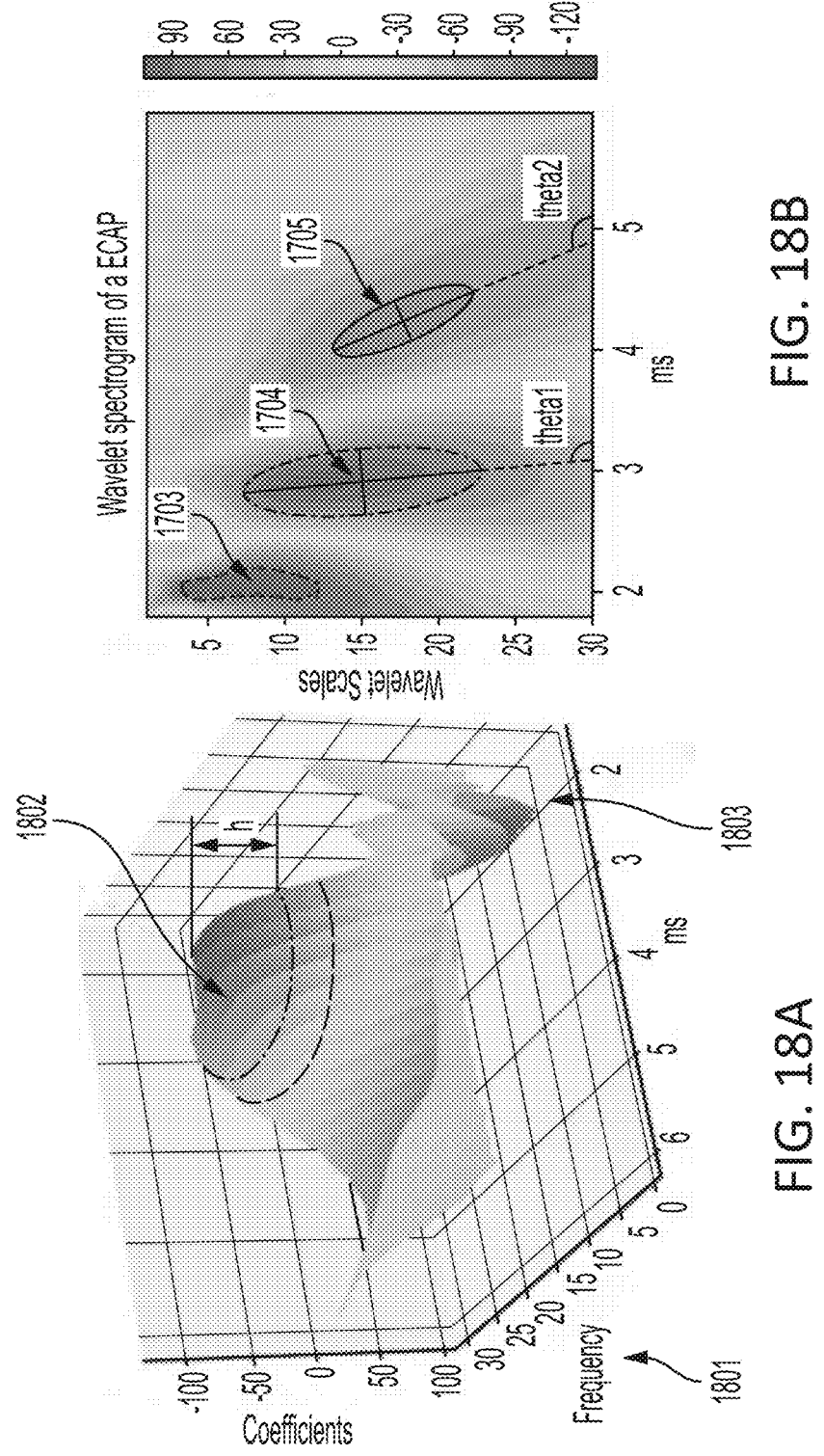

The two-dimensional array of data is subjected to closed-contour analysis and/or other segmentation processing to extract ECAP related features in the data (1603 in FIG. 16). Specifically, the ECAP component of the data is discernably as discrete phases at different temporal-frequency space locations. For example, the graph of FIG. 17B includes closed contours 1703, 1704, and 1705 which each correspond to respective phases of the ECAP response of the patient to the electrical pulses. FIGS. 18A-18B depict respective graphs of the same data in the frequency-temporal domain in which a three-dimensional graph 1801 of the amplitude versus time and frequency is provided by projecting into a graph format, as shown in FIG. 18A. Upon ECAP feature identification, the longitudinal and time axis angle of each closed contour 1802, 1803 may be extracted (as shown in FIG. 18A-B). The estimated time duration of each corresponding ECAP feature can be estimated from the identified closed contour features in the frequency-temporal domain data.

2D signal segmentation techniques may be employed to extract the closed-contours that contain relevant ECAP related data. Suitable signal segmentation techniques include thresholding, clustering, histogram-based filtering, edge-detection, regional property-based detection, or machine-learning & computer vision-based methods. Both, semantic and instance segmentation methods, may be employed to identify all contours and accurately classify them. Additionally, information about the contour shape is integrated to facilitate classification of regions as signals of interest versus noise (ex: circularity, eccentricity, etc.).

After initial segmentation processing, we can further extract related features to help further screening which features could be ECAPs signal or the targeted signal we are interested in. For example, extraction of amplitude-based features, the angle between the longitudinal axis and the time axis, the duration of the closed contour of the ECAPs like signal, etc. These features can be used to compare to or measure against known features or profiles of ECAP signals, and then further rule out those extracted features that are not ECAP-related or our target signals of interest.

Figure 19B:
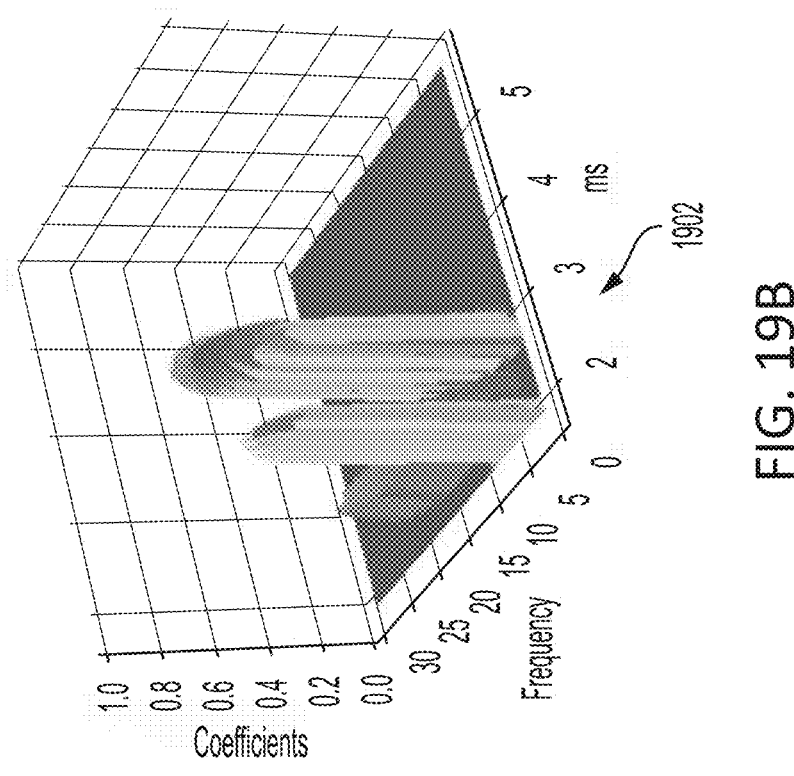
Figure 19A:
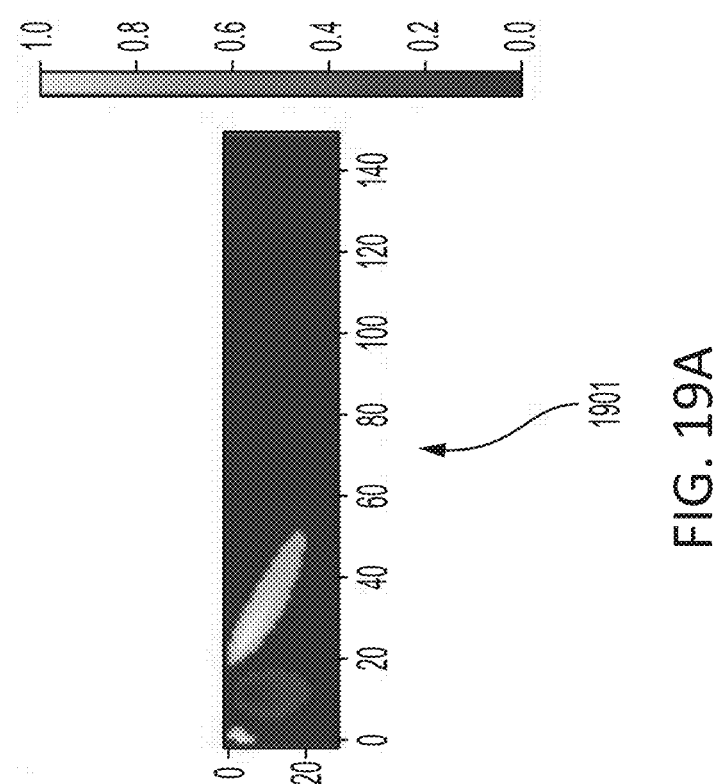
Figure 20B:
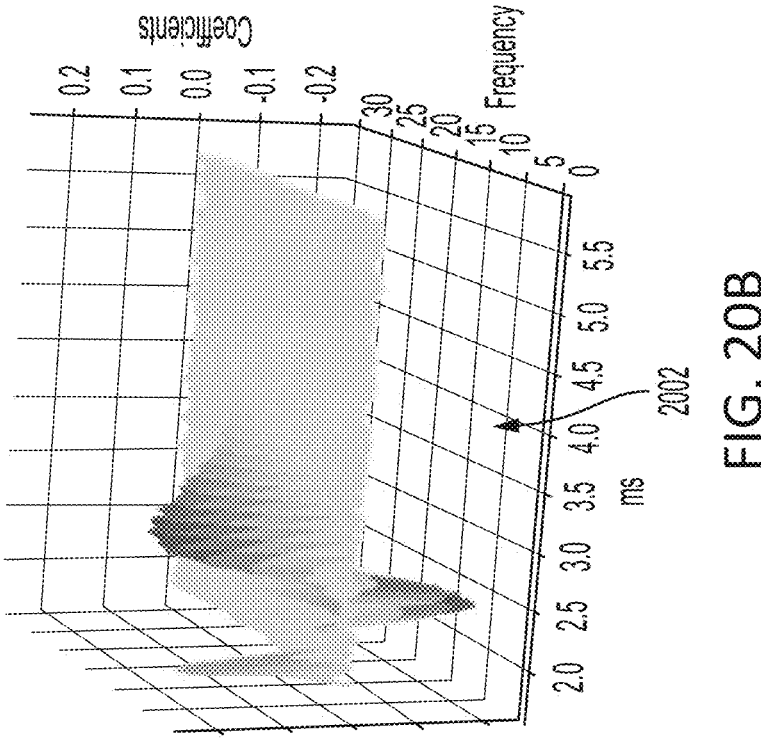
FIGS. 20A-20B depicts isolated ECAP features with surrounding areas masked with Gaussian noise according to some embodiments.
Figure 20A:
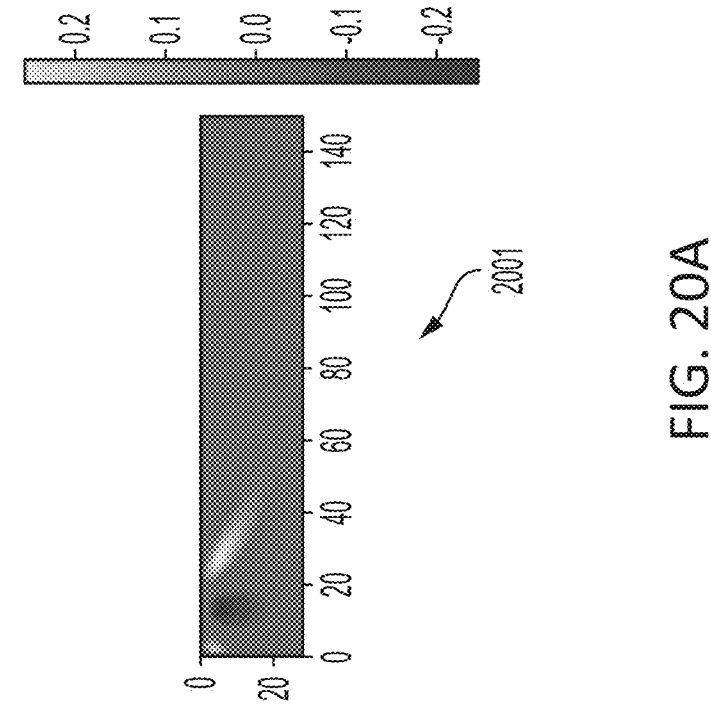

Referring to FIGS. 19A and 19B, graph 1901 depicts segmentation of the different phases of the ECAP response of the patient to the electrical pulse with graph 1902 representing a 3-D graph of the frequency coefficients from the segmented data. After segmentation, processing of the remaining data may occur. The frequency coefficients for each segmented feature may be resetttled with the base of each feature begin set to zero. Additionally, the remaining data points in the 2-D frequency-temporal domain that are not associated with one of the segmented ECAP features (i.e., zero data points) are masked with Gausian noise, as shown in graphs 2001 and 2002 of FIGS. 20A-20B.

Figure 21:
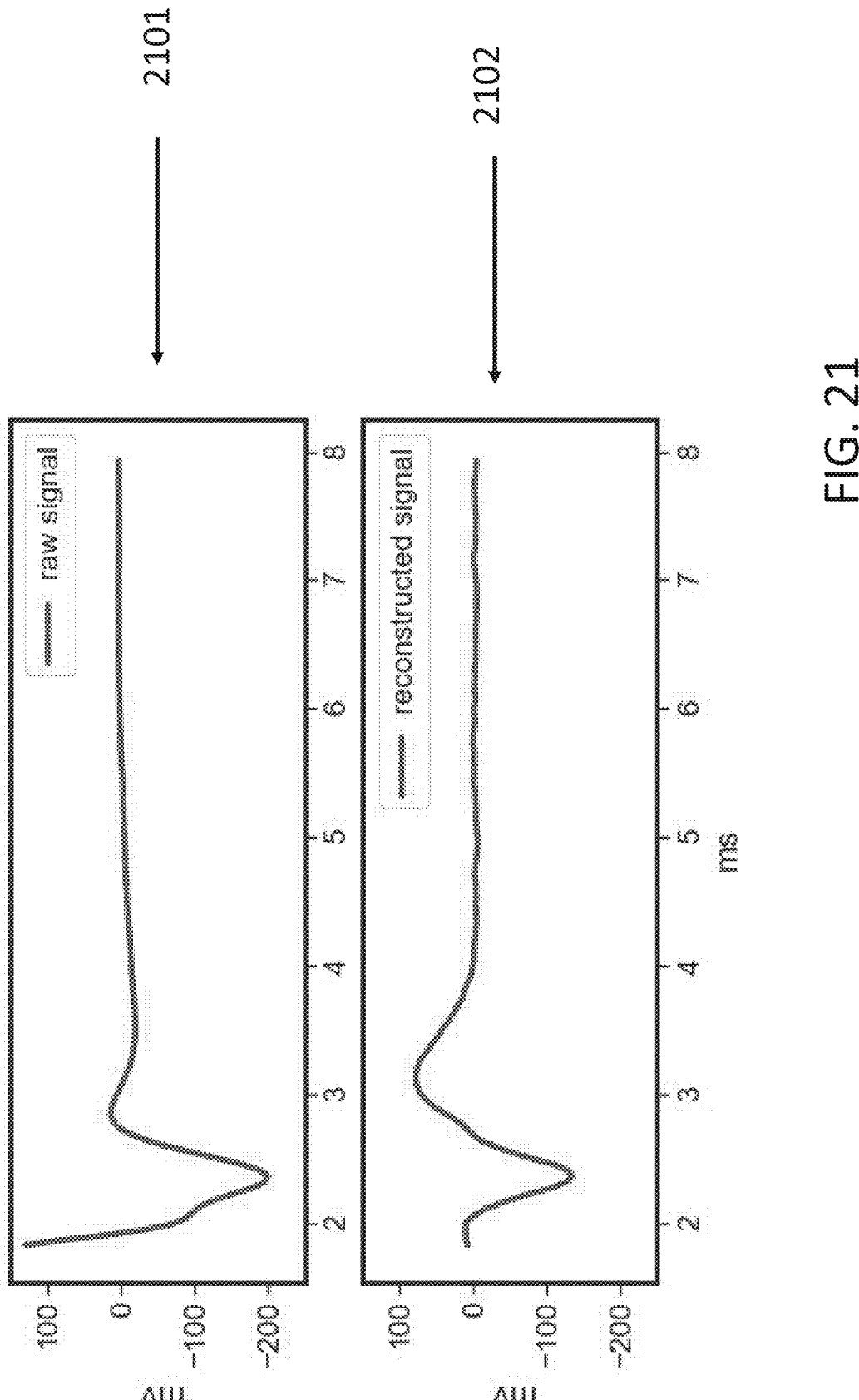
FIG. 21 depicts raw signal data obtain by sensing circuitry of an IPG and a graph represents processing for a reconstructed signal that represents the segmented ECAP features according to some embodiments.

Referring to FIG. 16, the 2-D array of data in the frequency-temporal domain corresponding to extracted ECAP features is converted back into time domain. Any suitable transformation processing may be employed. The conversion may include application of a 2D kernel to smooth the signal and then transformation of the data into a one dimensional time series. Alternatively, the conversion may include transformation of the data into a one dimensional time series and then application of a 1D kernel to smooth the signal. Referring to FIG. 21, graph 2101 represents raw signal data obtain by sensing circuitry of an IPG and graph 2102 represents processing of the signal as discussed herein to generate the reconstructed signal that represents the segmented ECAP features.

Referring again to FIG. 16, in 1606, the reconstructed signal is analyzed (as discussed herein) to determine whether any appropriation action should be taken and, if so, the patient's neurostimulation therapy is modified and/or an alert is provided to the patient and/or the patient's clinician (1607).

The processing of ECAP data into a temporal-frequency domain may be used for any number of applications to assist neurostimulation therapies. In some embodiments, this analysis is conducted while a clinician implants one or more stimulation leads within a patient during a medical procedure. For example, the position of a stimulation lead is an important factor for successful neurostimulation therapy. If the stimulation is incorrectly positioned, the proper dorsal fibers of the spinal cord may be stimulation by electrical pulses applied through electrodes of the lead. Alternatively, the electrical pulses may stimulation unwanted neural tissue causing unwanted side effects (e.g., muscle stimulation or painful/uncomfortable sensory effects).

Figure 25:
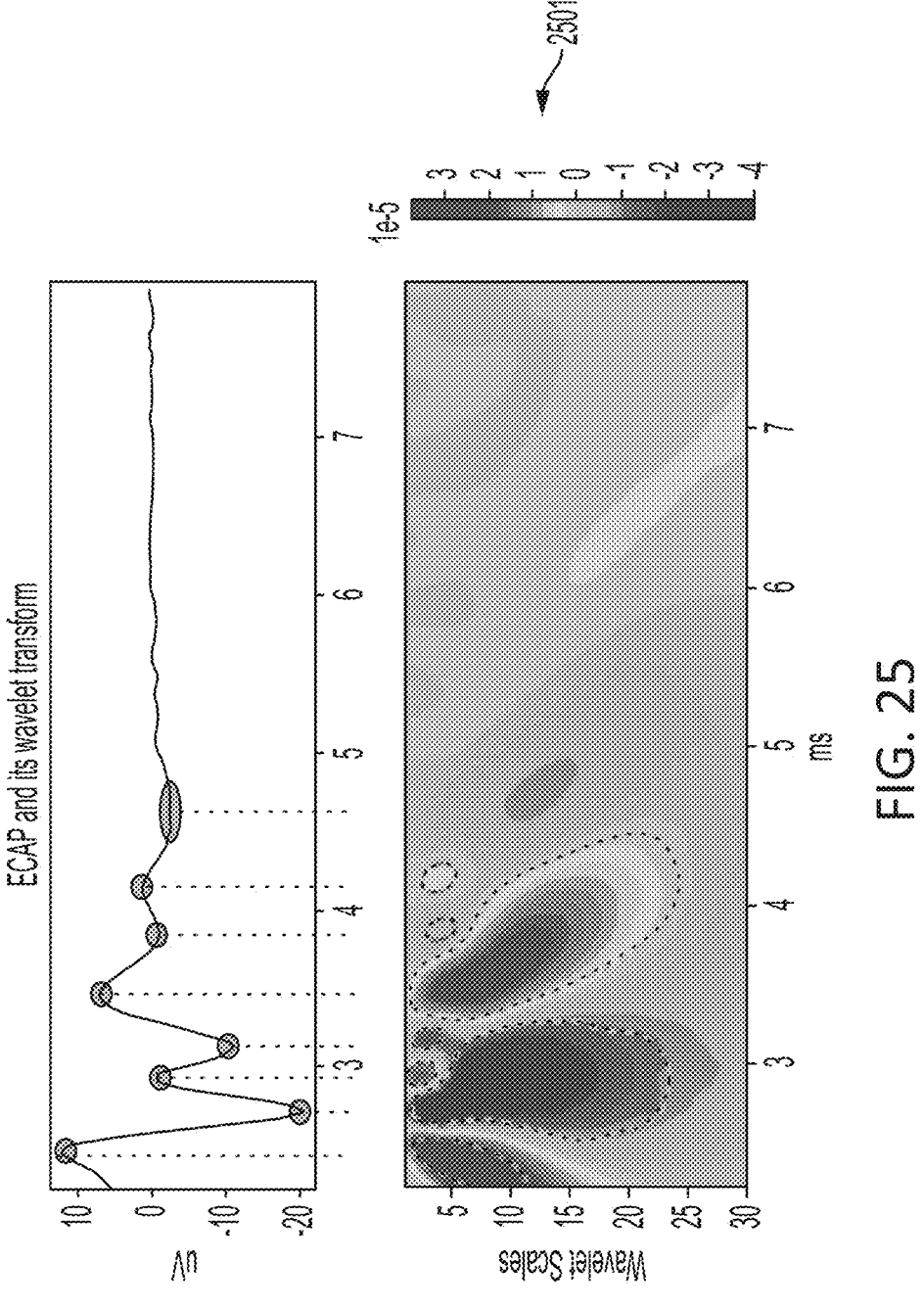
FIG. 25 depicts an ECAP display according to some embodiments.

FIG. 25 depicts ECAP display 2501 according to some embodiments. As seen in display 2501, the ECAPs signal exhibits a complicated multiphasic morphology (as compared to the morphology of the ECAP signal seen in FIGS. 17A-17B). ECAP display 2501 was created by stimulating, measuring the patient response using a suitable electrode, and processing the signal as discussed herein (including the processing operations described with respect to FIG. 16). The display of the morphology shown in ECAP display 2501 may indicate unexpected activation in response to the stimulation (which might indicate the activation of muscle activity). When such a response is seen by the clinician during an implant procedure, the clinician may reposition one or more the stimulation leads before completing the implant procedure with the lead or leads in their final position.

Figure 26:
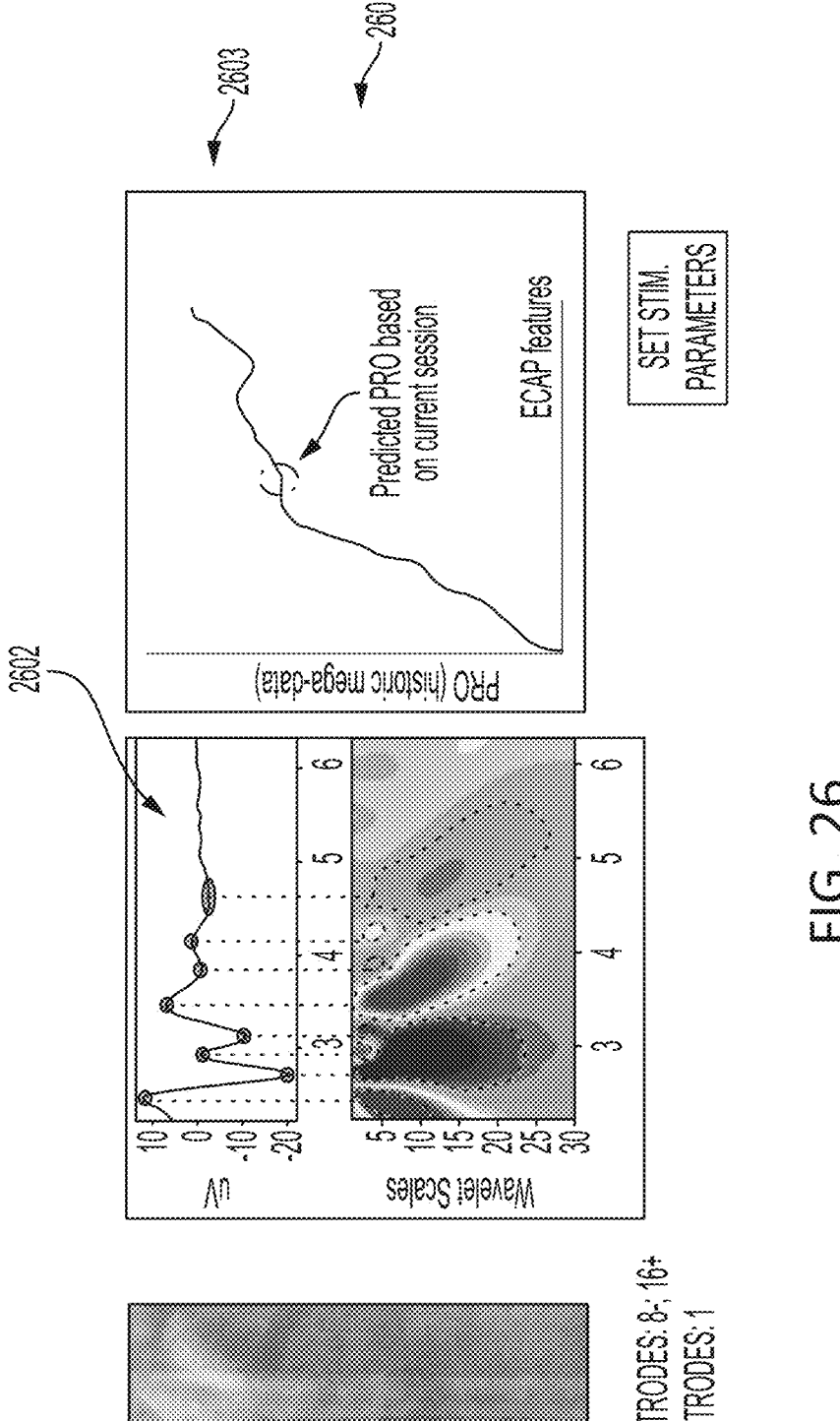
FIG. 26 depicts an exemplary clinician user interface for display of ECAP data to assist an implant procedure according to some embodiments.

Clinician user interface 2601 (in FIG. 26) depicts display of ECAP data to assist an implant procedure according to some embodiments. Clinician user interface 2601 may be provided using a clinician programming device as discussed herein using a clinician "app" on the device. Clinician user interface 2601 may display a medical image of the patient with the position of the leads shown relative to the patient's anatomy. The medical image may be a virtual construction for the position or a direct image from medical imaging technology (e.g., a fluoroscopic imaging system). Clinician user interface 2601 may display the electrode(s) used for stimulation and recording operations. Clinician user interface 2601 may include a graphical user control element to switch to conventional programming screens (to set stimulation settings, e.g., amplitude, frequency, pulse width, etc.). Clinician user interface 2601 depicts ECAP data in the time domain and in the temporal/frequency domain as discussed herein as shown in ECAP display 2602. The implanting clinician may view ECAP display 2602 to ensure that the expected patient response to the stimulation is obtained at the implant position.

In some embodiments, ECAP measurement and objective analysis will be conducted real time during an implant procedure. The ECAP results will be displayed alongside the fluoroscopy image to provide guidance for physicians during the implantation process. In some embodiments, clinician user interface 2601 may also provide a predicted patient reported outcome ("PRO") based on the current signals that the system is measuring during implantation process. The predicted may be conducted by a mathematical model that is trained based on historical offline data. During the implantation process, the newly measured ECAP signal will be feed into the model, and a predicted PRO outcome in PRO graph 2603 will be shown to inform physician about the effectiveness of the stimulation applied to the patient. This predicted PRO, together with ECAPs signal visualization, will be used to provide quantitative analysis real time during the implantation procedure.

The PRO could be any patient reported outcome data from historical sessions from the same or other patients. The PRO data could consist of any type of patient reported outcome including, but not limited to, patient reported score, quality of life assessment score, paresthesia information from historical session or during the session reported by the patient, etc. The features used to train the model offline and conduct prediction during the actual implantation process could include ECAPs signal and its derived features, other types of physiological data recorded during a implantation session, such as somatosensory evoked response, ECG, EEG, etc. The features might also use patient reported results to feed in as an input to the model, based on how the predicted PRO is defined.

Figure 22A:
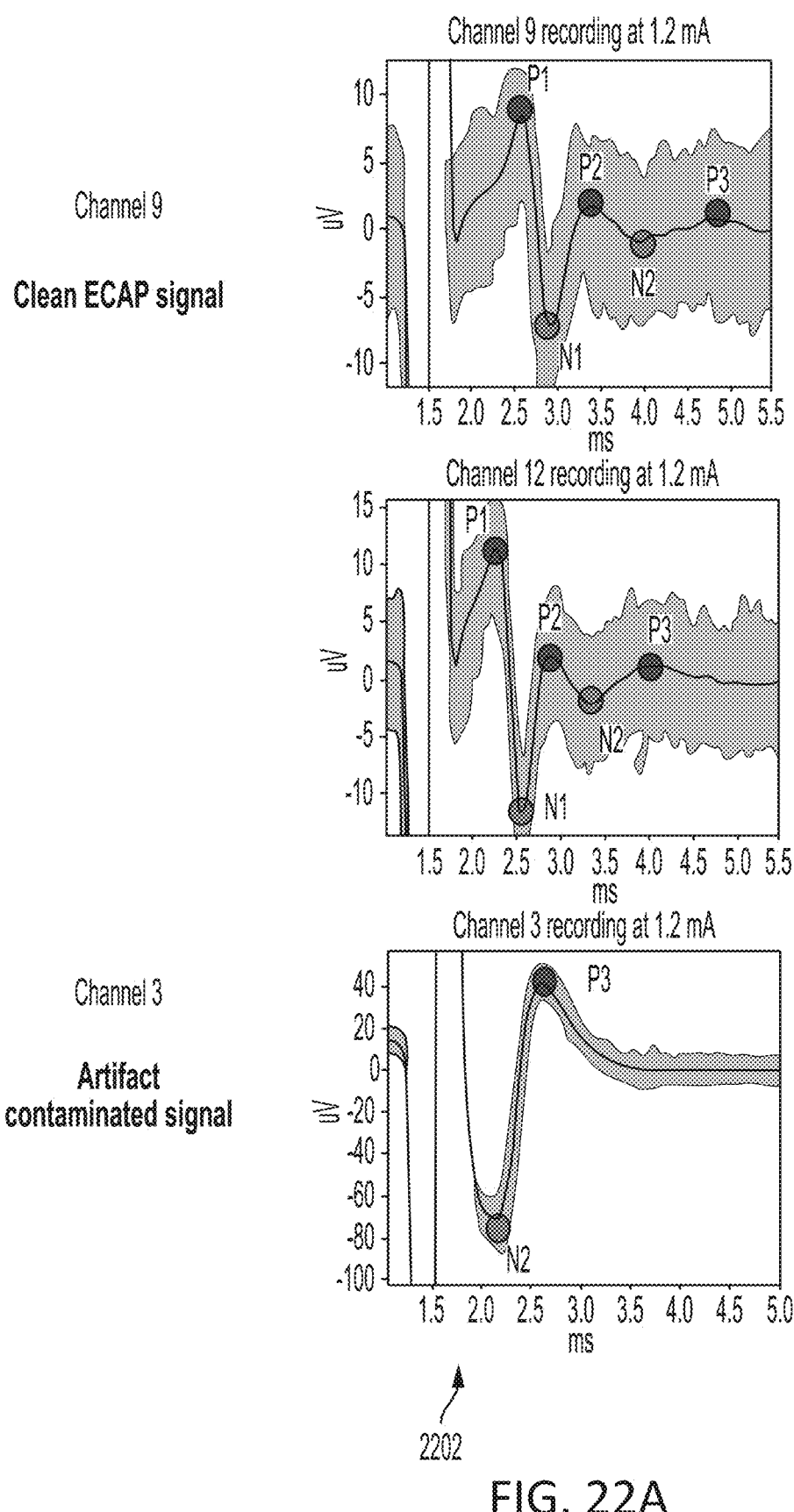
FIGS. 22A-22C depict ECAP and stimulation artifact signals and FIG. 23 depicts a patient system computational model to allow recovery of ECAP features from a sensing electrode according to some embodiments.
Figure 22B:
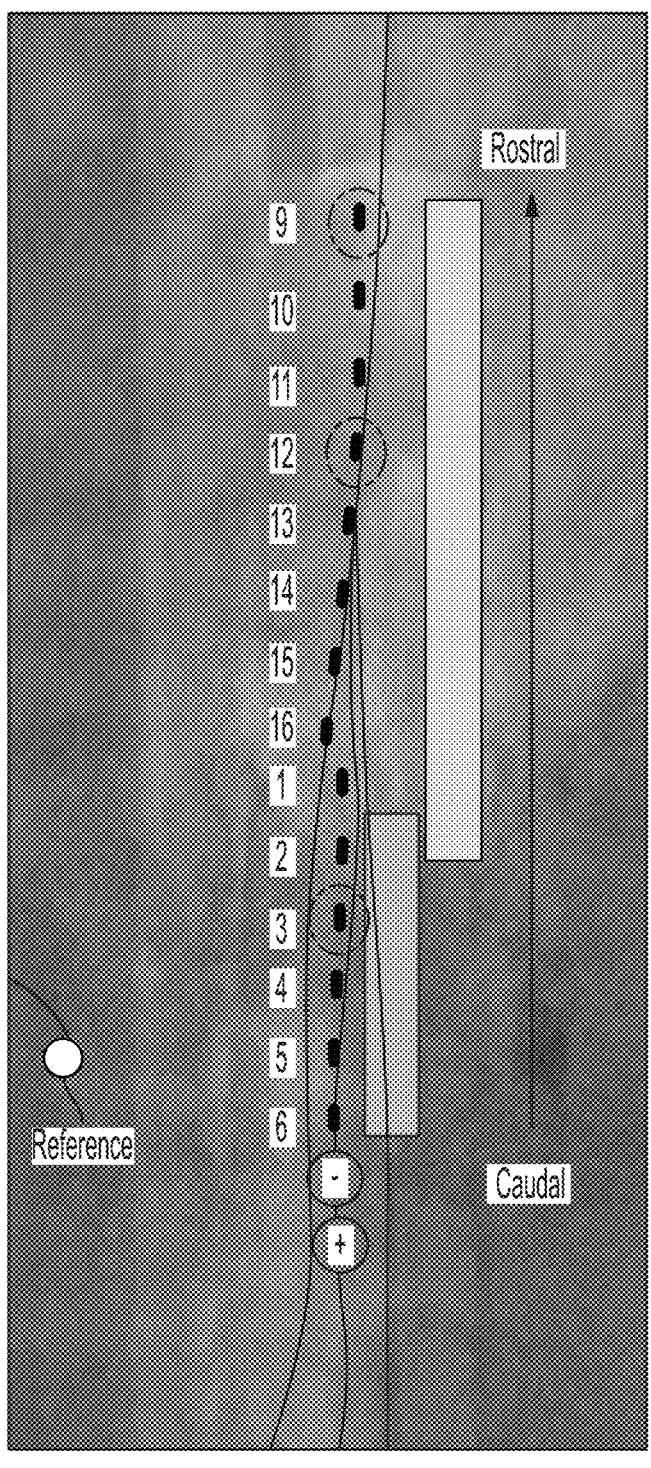
Figure 22C:
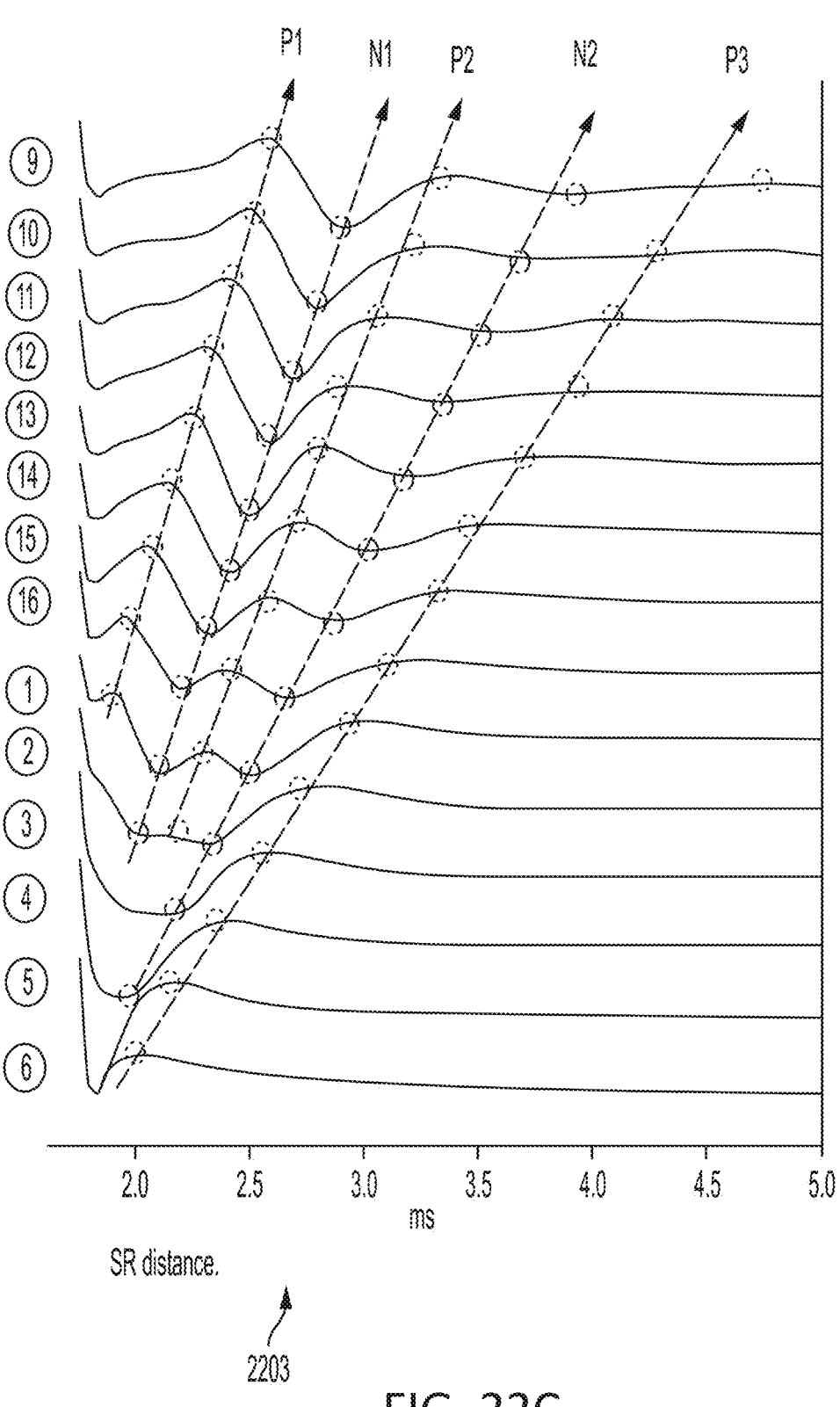

In other embodiments, samples of sensed data in response to electrical pulses applied to the patient may be subjected to other processing to remove stimulation artifact recovery features from ECAP features in the sensed data. FIGS. 22A-22C depicts ECAP data related to stimulation on caudal electrodes and sensed data using electrodes rostral to the stimulation electrodes. As shown in lead configuration 2201 in FIG. 22B, two percutaneous leads are implanted in the epidural space of the patient. The electrodes of the two leads are roughly placed in a linear, sequential order. The percutaneous leads are placed such that the most distal electrode ("electrode 1") of the first lead is immediately caudal to the most proximal electrode ("electrode 16") of the second stimulation. Electrodes 7 and 8 (with polarities of "−" and "+") are used to apply stimulation pulses from the IPG to dorsal fibers of the patient's spinal cord.

Now, because electrode 9 of the second stimulation lead has sufficiently spatial separation from electrodes 7 and 8 of the first stimulation lead, it is possible to measure a clean ECAβ signal. However, in channel 3 which is located very close from the stimulation channels, only artifact contaminated signal can be measured in certain circumstances. The stimulation artifact and artifact recovery features propagate more rapidly than the ECAP features. For sensing electrodes closer to the stimulation electrodes, there is overlap of the respective features in time. With electrodes with greater separation, there is sufficient temporal separation between features to allow ready identification of the separate features as represented in the timing graph 2203 of FIG. 22C.

As shown in sensed data graphs 2202 of FIG. 22A, the ECAP features including the multiple positive phases (P1, P2, and P3) and negative phases (N1 and N2) are identifiable from the sensed data using electrode (or channel) 9. However, for electrode (channel) 3, the sensed data is largely dominated by the artifact/artifact recovery features from the applied electrical pulse and, hence, the ECAP features are hidden in the sensed data from electrode 3.

Figure 23:
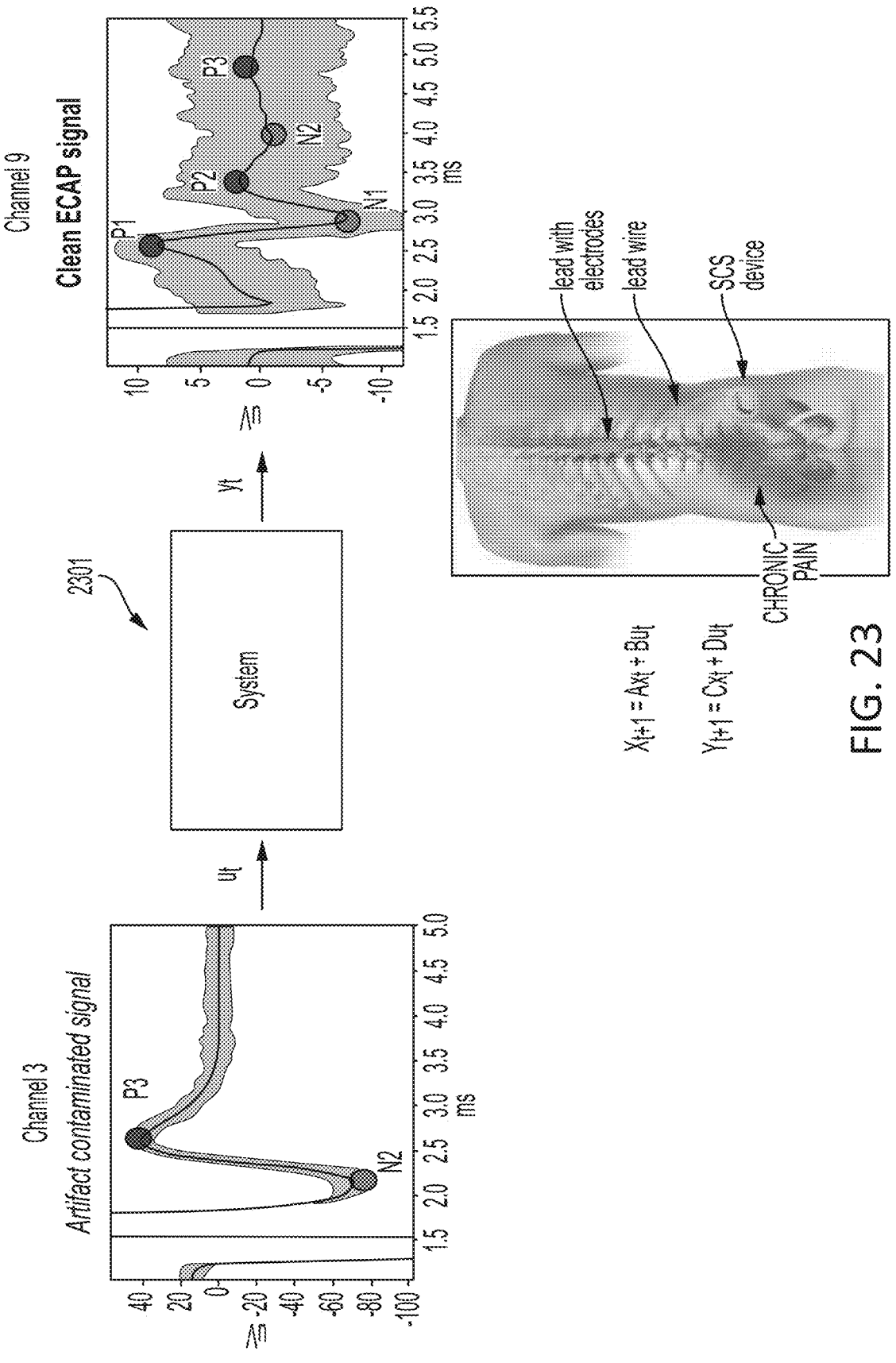

As shown in FIG. 23, a patient system computational model is created to allow recovery of ECAP features from a sensing electrode that is relatively close to one or more stimulation electrodes. As seen in computational relationships 2301 of FIG. 23, the signal of electrode/channel 3 (that is contaminated by stimulation artifact/recovery features) is defined as the input of the patient system and the signal sensed by electrode/channel 9 (which has clean ECAP signal) is defined as the output of the system. The patient system can be represented as a transfer function. To perform system identification to find a transfer function model, a state-space model is defined by matrices A, B, C and D. These matrices can be solved from the input and output signals by utilizing the Eigensystem realization algorithm (ERA) may be applied. Upon determination of these matrices A, B, C, and D, the system is characterized and, then, can be applied to subsequent data samples to obtain the ECAβ features from a signal contaminated with stimulation pulse artifact/recovery features. That is, using the state-space model, it is possible to estimate output yt (clean ECAP signal) from input ut (artifact contaminated signal).

Figure 24:
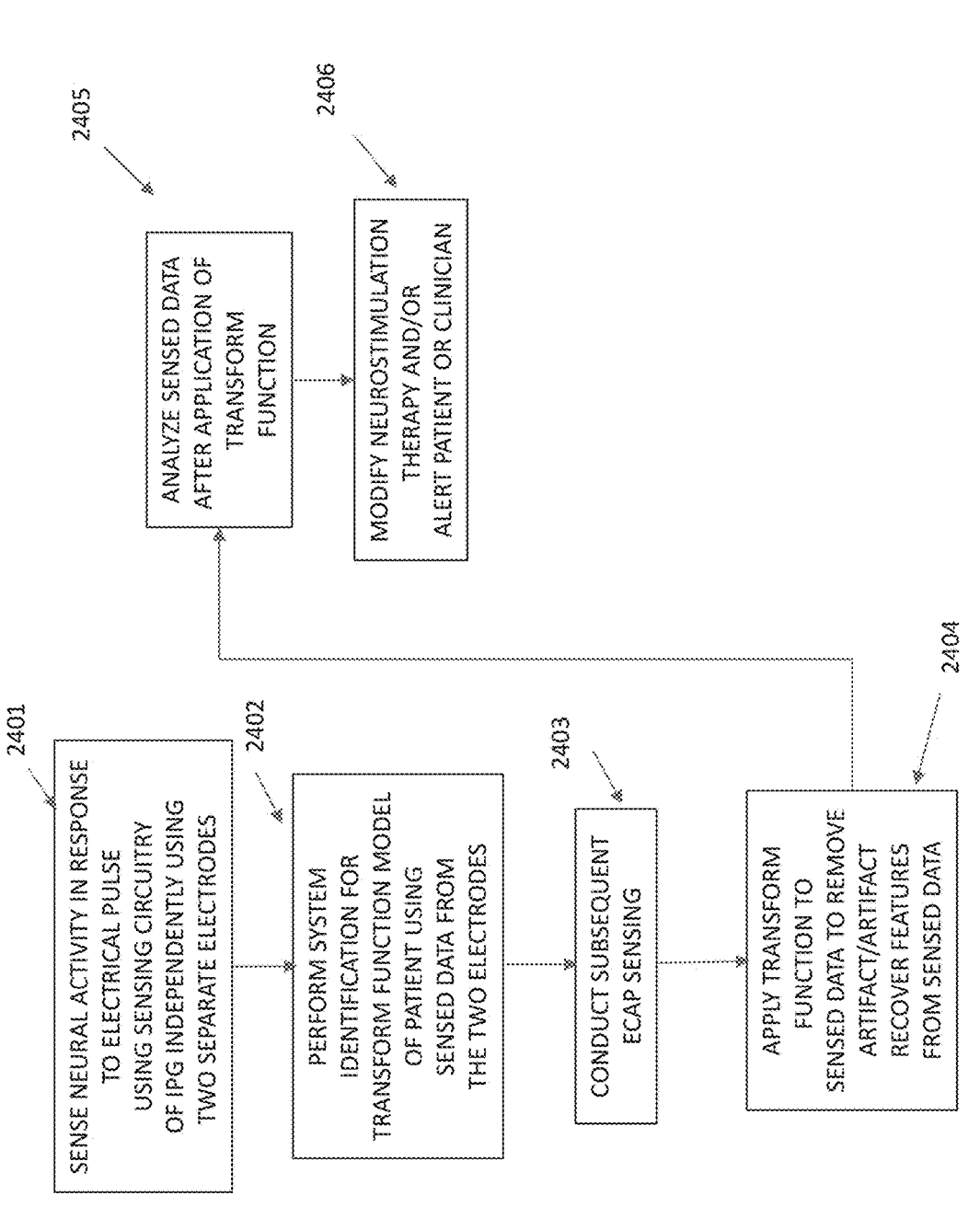
FIG. 24 depicts operations for conducting ECAP sensing operations for a neurostimulation system according to some representative embodiments.

FIG. 24 depicts operations for conducting ECAP sensing operations for a neurostimulation system according to some representative embodiments. In 2401, neural activity in response to an electrical pulse is sensed using circuitry of IPG using two separate electrodes. In 2402, system identification operations are performed using the sensed data from the two electrodes. The system identification operations determine a transform function that transforms that time series data sensed using the first electrode into the time series data sensed using the second electrodes. In 2404, the transform function is applied to subsequently sensed data to remove artifact and/or artifact recovery features from the sensed data. In 2405, the sensed data after application of the transform function is analyzed using suitable ECAP analysis operations. In 2406, the neurostimulation therapy of the patient is modified and/or an alert is provided to the patient and/or the patient's clinician.

In some embodiments, ECAP analysis is applied to detect migration of one or more stimulation leads after implantation into a patient. The detection of migration may detect relative movement of one stimulation relative to another stimulation lead. In other embodiments, detection of migration of a stimulation lead may detect migration of a stimulation lead relative to an anatomical structure of the patient. In addition, the migration (in either case) may be transient. For example, the position of the leads and/or their respective electrodes may change based on patient posture and some embodiments detect such changes. The detected change may be used to infer patient posture, position, activity, and/or the like and stimulation may be modified as appropriate.

Figure 27A:
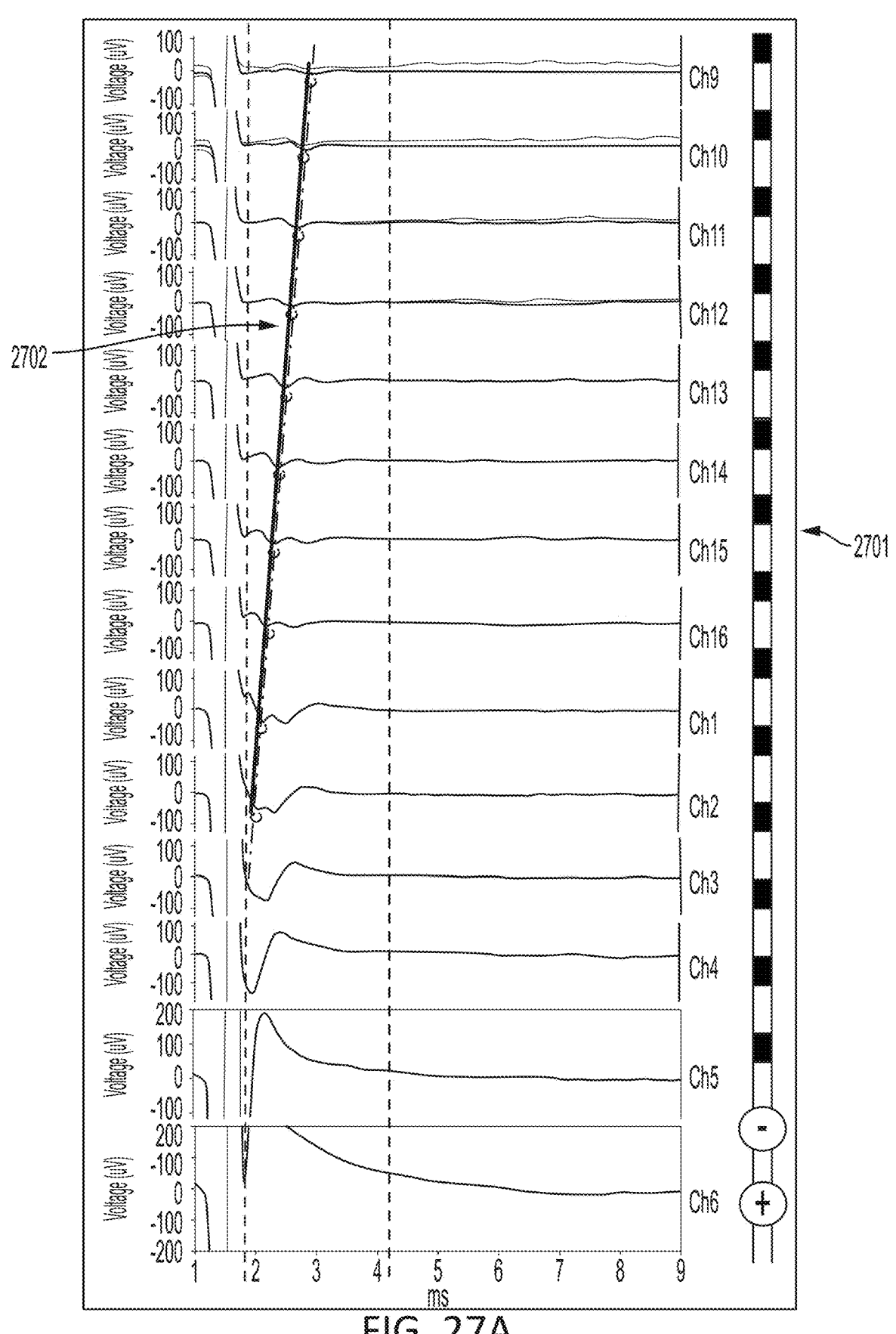
FIGS. 27A-27B depict the propagation of ECAP from stimulation electrodes occurring rostrally along respective recording electrodes along the depicted stimulation lead for processing according to some embodiments.
Figure 27B:
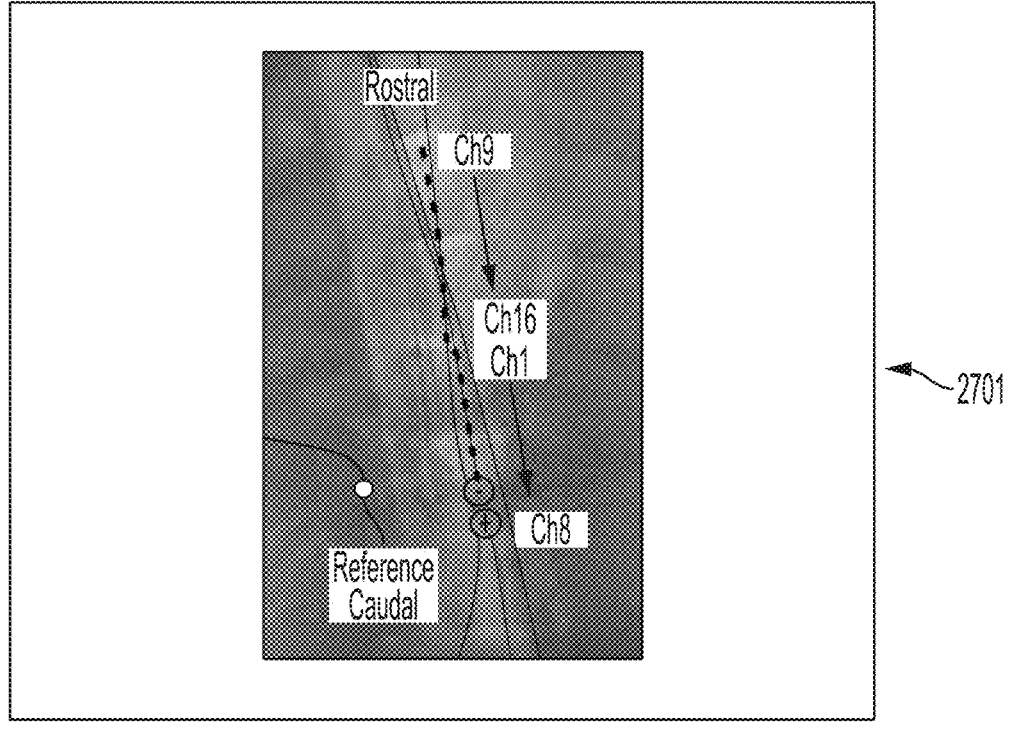

FIG. 27A-27B depict the propagation of ECAP from stimulation electrodes occurring rostrally along respective recording electrodes along the depicted stimulation lead. As shown in FIG. 27A, electrodes of channels 5 and 6 (shown as Ch5 and Ch6) are used as a bipolar pair (one negative and one positive electrode) for application of a stimulation pulse. The electrical pulse causes an ECAβ and the ECAP propagates through the neural tissue. In this case, Ch1-Ch4 of the same stimulation lead and Ch9-16 of a second stimulation lead positioned substantially parallel and rostrally to the first stimulation lead can be used to measure the propagating ECAP The detected waveform including the ECAP is shown in time adjacent to each electrode of channel. Line 2702 shows the beginning of the ECAP feature in time as detected by each respective electrode or channel. Near the stimulation site (more caudally), the evoked response has shorter latency from the stimulation artifact, while away from the stimulation site (more rostrally), the evoked response has longer latency from the stimulation artifact.

In some embodiments, the ECAP signal can be used to detect the relative position of multiple leads (e.g., two stimulation leads commonly implanted). Stimulation is initiated by one of the implanted leads and ECAP neural recordings are recorded on the other lead. Across multiple contacts of the leads, ECAPs signals will present different phase shift or latency depends on the location (as shown in FIG. 28A).

Figures 28A, 28B:
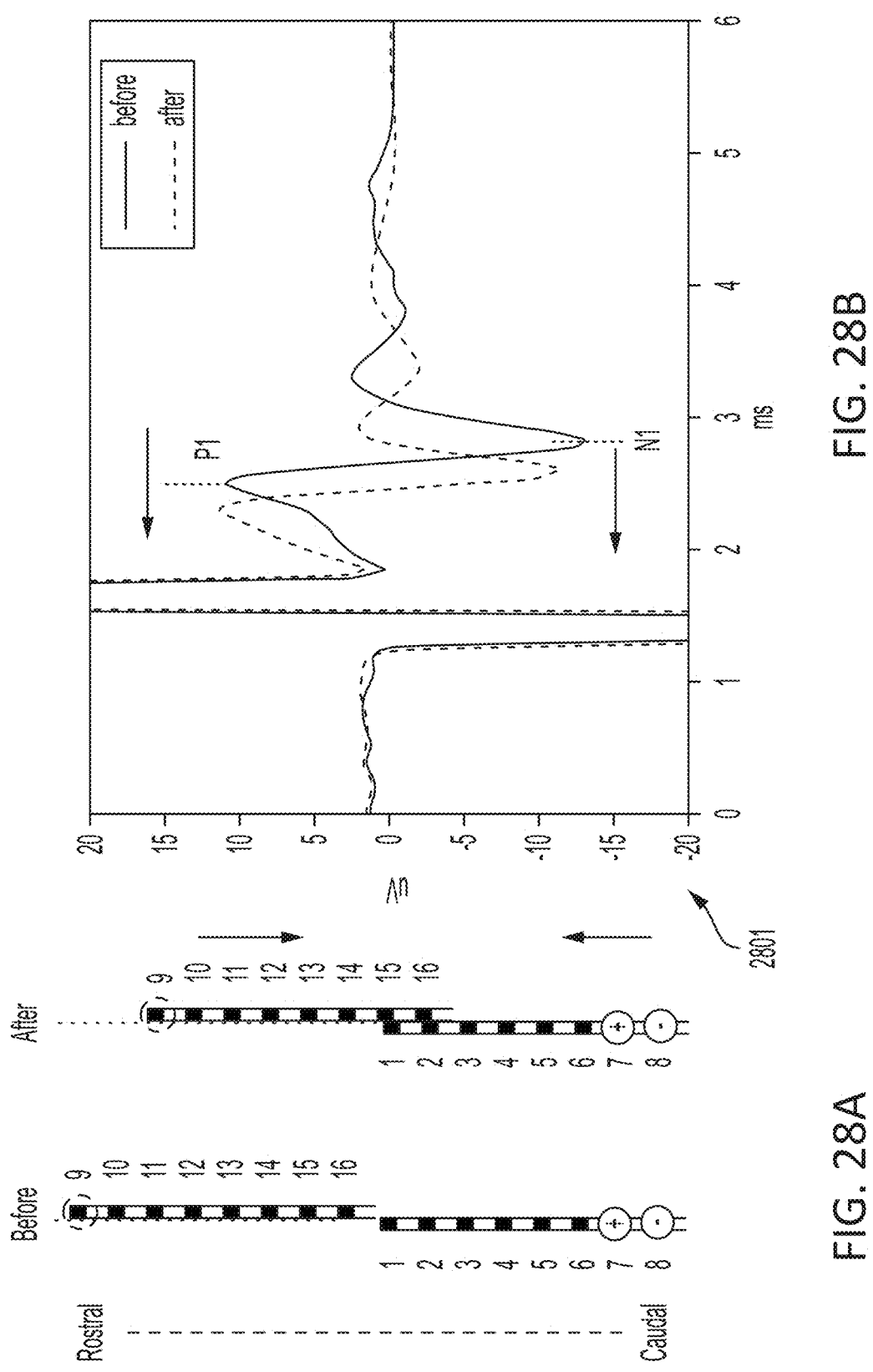
FIGS. 28A-28C depict aspects of a phase shift or latency change for processing according to some embodiments.
Figure 28C:
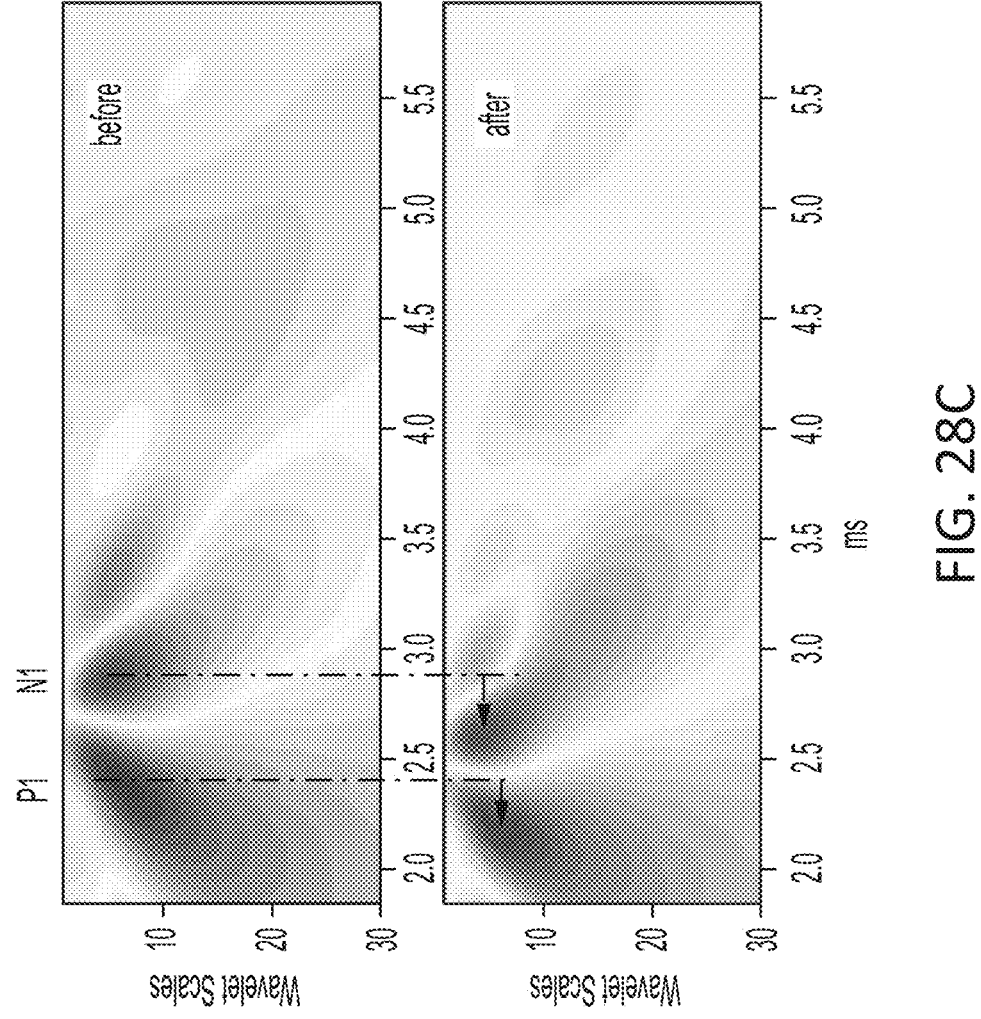

FIGS. 28B-28C illustrate aspects of a phase shift or latency change for processing according to some embodiments are shown. The phase shift or latency change could be viewed in both time domain in regular time series data, or it can be viewed in the transformed domain, as shown in graph 2801 of FIG. 28B and in FIG. 28C, respectively. The example shows the transformed domain as the scalogram of using wavelet transform applied on the original time series recording. The methodology used in such transform could also include any other similar signal processing methods, such as Fourier Transform based methods (FFT, DTFT), Hilbert Transform based methods (HHT), which can generate any spatial-temporal, frequency/scale-temporal signal map to visualize the latency change.

In one example, the latency of the ECAPs recording (as shown in FIGS. 27A-27B) indicates the distance between the two leads. In this manner, a diagnostic can be run when the subject is known to be in a particular position (e.g., lying down when sleeping) and the latency of the ECAβ neural signal following the stimulation pulse, as indicated at 2702, may be used to determine the relative position of the two leads in the rostro-caudal direction. For example, given any contact on the recording lead, if with decreasing latency at different time of measurements, the rostral lead is moving more caudally or the caudal lead is moving more rostrally. Similarly, if the recorded ECAβ signal is with increasing latency at different measurement time, it is likely that the rostral lead is moving rostrally, or the caudal lead is moving more caudally.

Figure 29A:
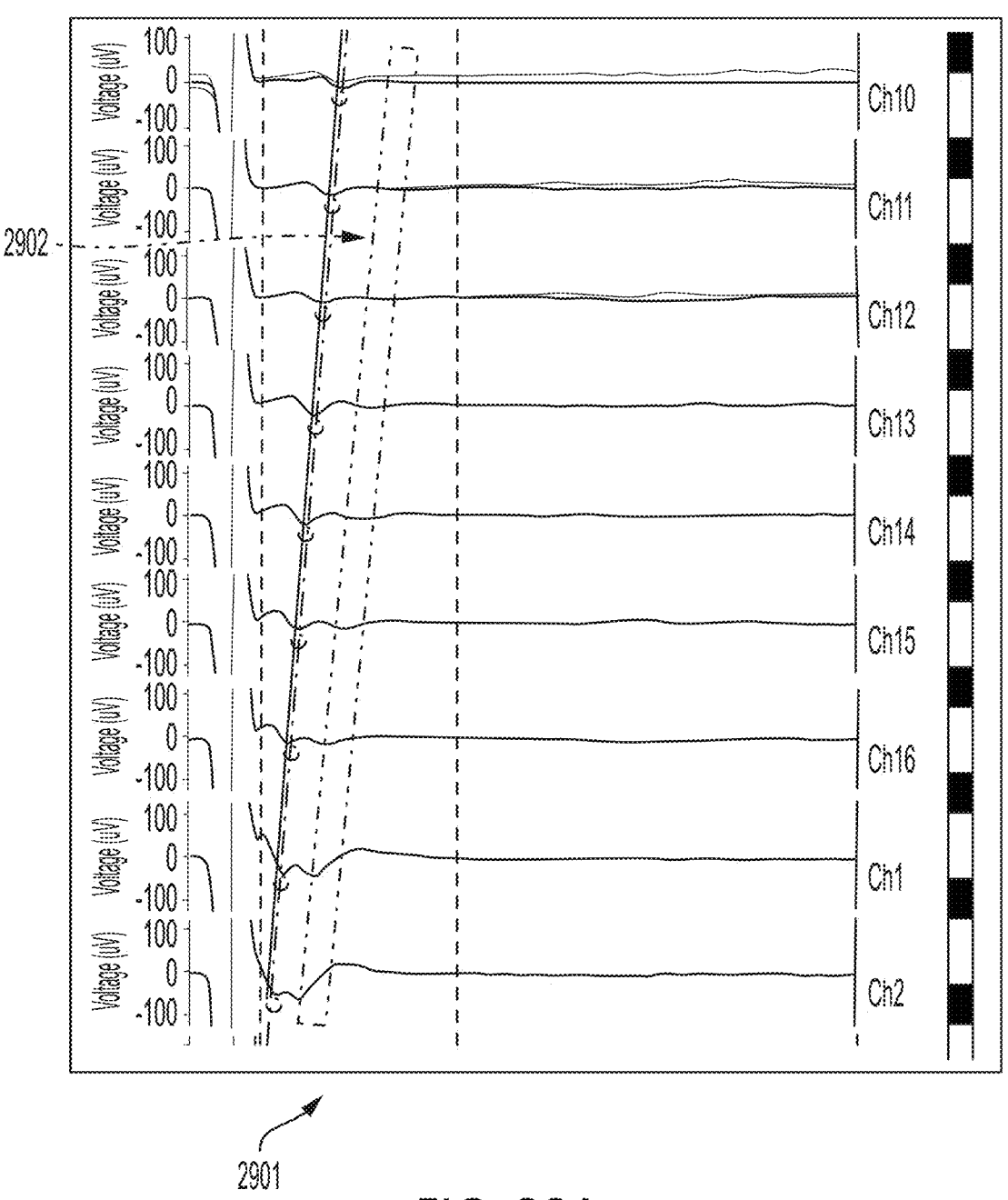
FIGS. 29A-29B depict aspects of the emergence and/or disappearance of a secondary phase of the ECAPs according to some embodiments.
Figure 29B:
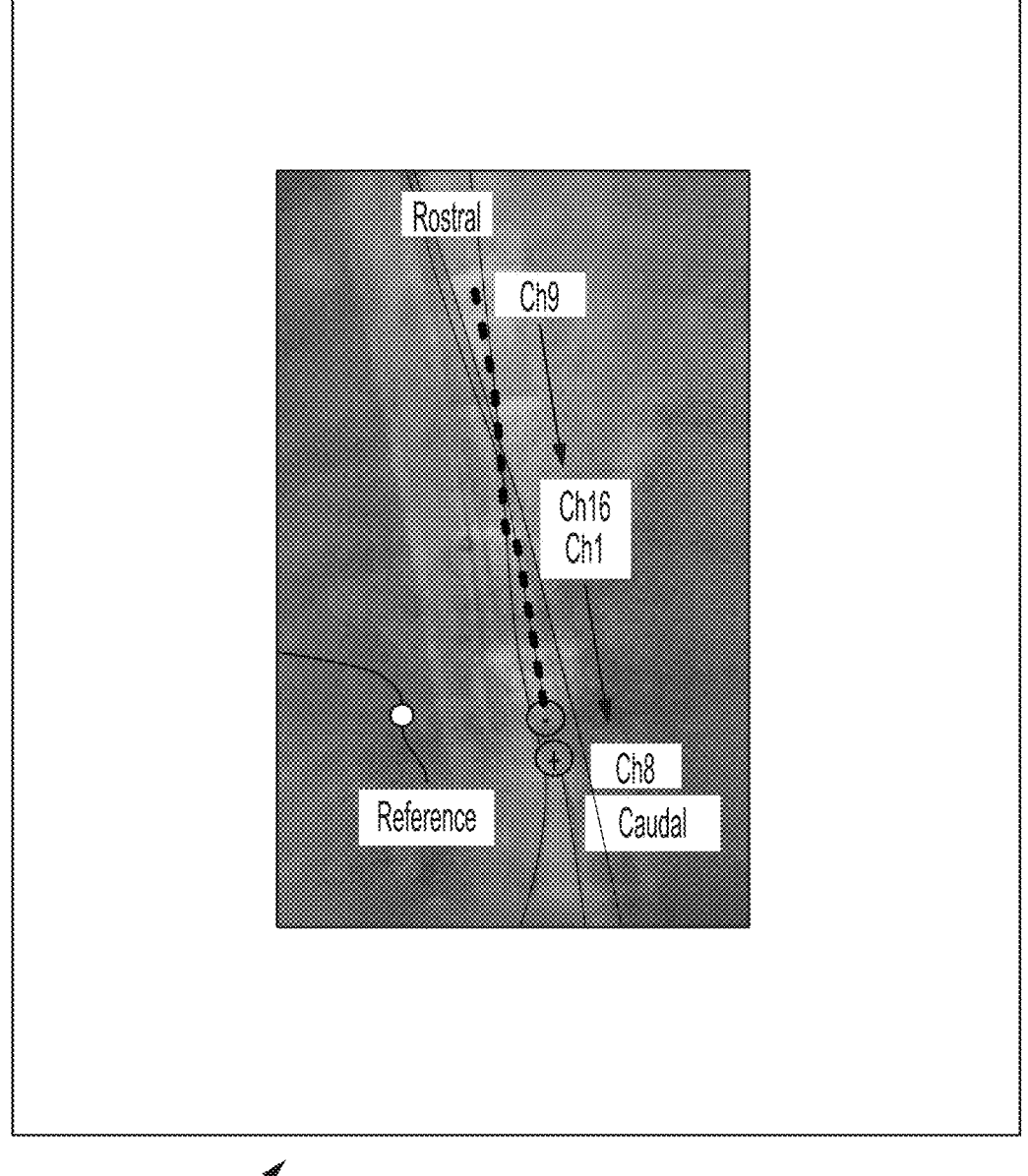

In another embodiment of the multiple leads implanted, the emergence and/or disappearance of a secondary phase of the ECAPs could happen as the recording contact is moving towards the stimulation location (as shown graph 2901 in FIG. 29A and FIG. 29B). In the case of emergence of new phase of ECAPs signal for a given contact, it indicates the rostral recording lead might moving more caudally, or the caudal stimulation lead is moving rostrally, as indicated at 2902. In the case of the disappearance of the secondary phase of the ECAPs signal, it indicates that the rostral recording lead might move more rostrally, or the caudal stimulation lead might move more caudally.

Figures 30A, 30B:
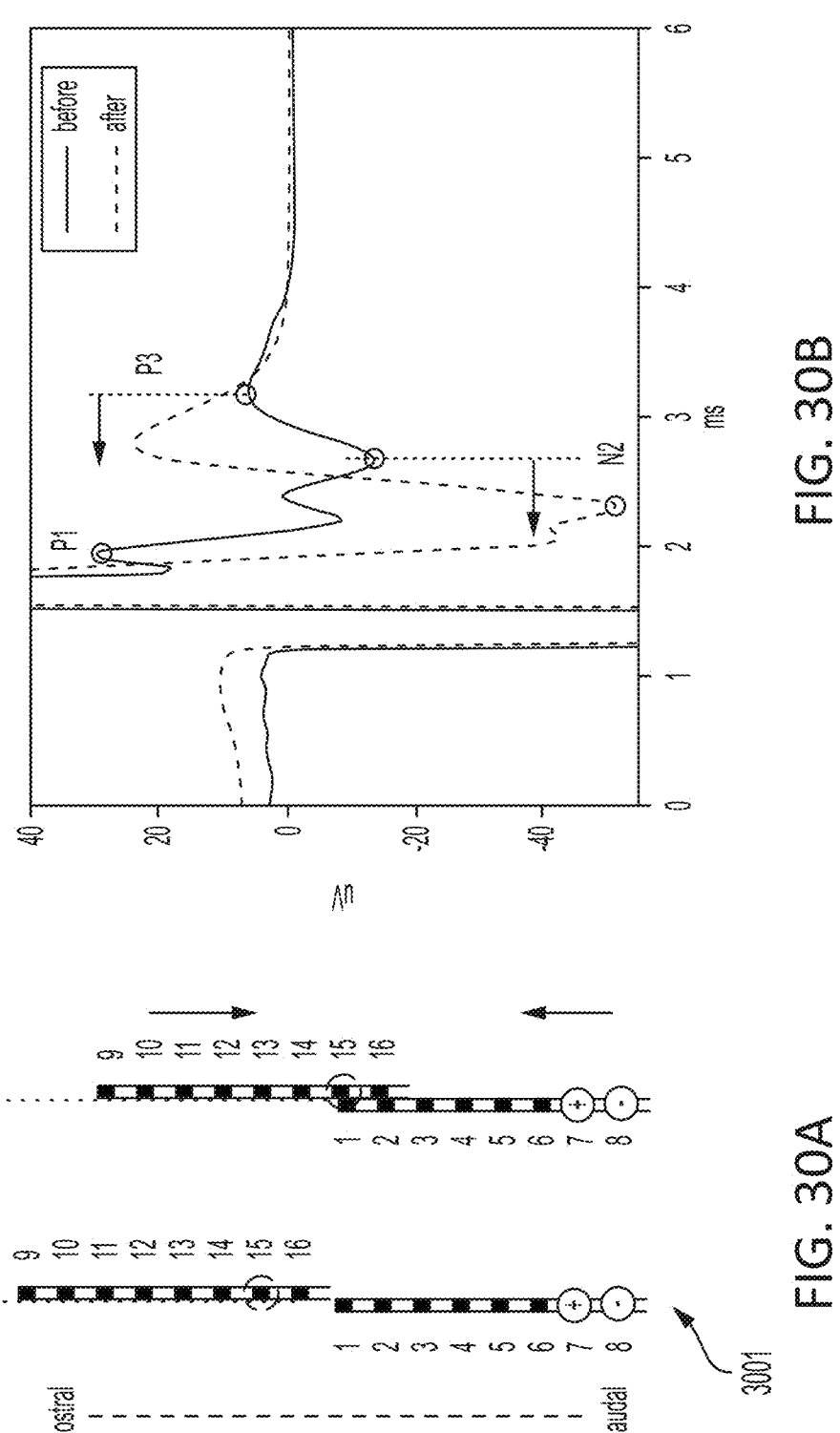
FIGS. 30A-30C depict aspects of the disappearance of a phase (P1) of ECAPs signal according to some embodiments.
Figure 30C:
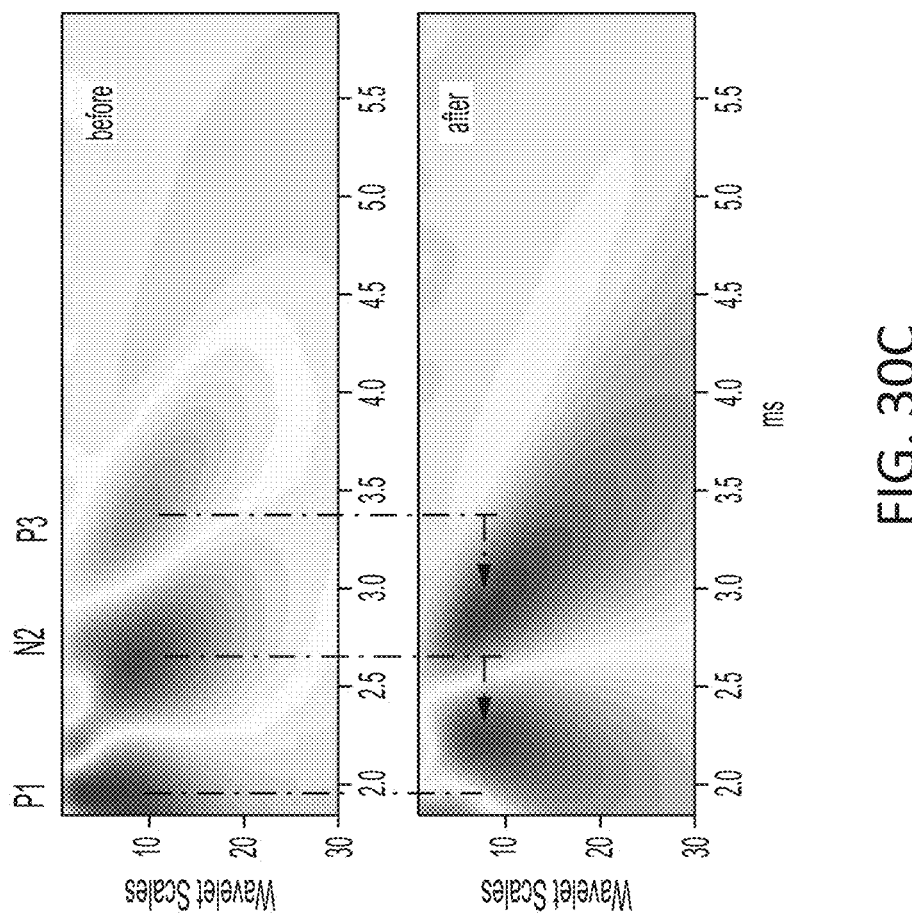

Referring to FIGS. 30A-30C, aspects of the disappearance of a phase (P1) of ECAPs signal are shown. FIG. 30B shows a graph illustrating the disappearance of the phase (P1) ECAPs signal. When two leads are moving towards to each other, as shown at 3001 in FIG. 30A, either recording lead is moving more rostrally, or stimulation leads is moving more caudally. The first positive peak (P1) from the same recording channel is completely disappeared after the lead has moved. The data may be observed in both time series (as in the graph of FIG. 30A) and scalogram (as shown in FIG. 30C).

As shown in the respective graphs, the timing of the phases (arrival, disappearance, etc.) can be identified in the time domain and/or in the temporal/frequency domain. The various techniques discussed herein may be applied to recorded data for the ECAP analysis.

The timing analysis discussed herein is not limited to application on the ECAPs signal that is recorded after the stimulation delivery. In the case of no ECAPs signal is being triggered, the waveform or its transformation of the artifactual recording could also be used to conduct the time domain or transform domain analysis to track if there is any signal latency or phase changes.

Figure 31:
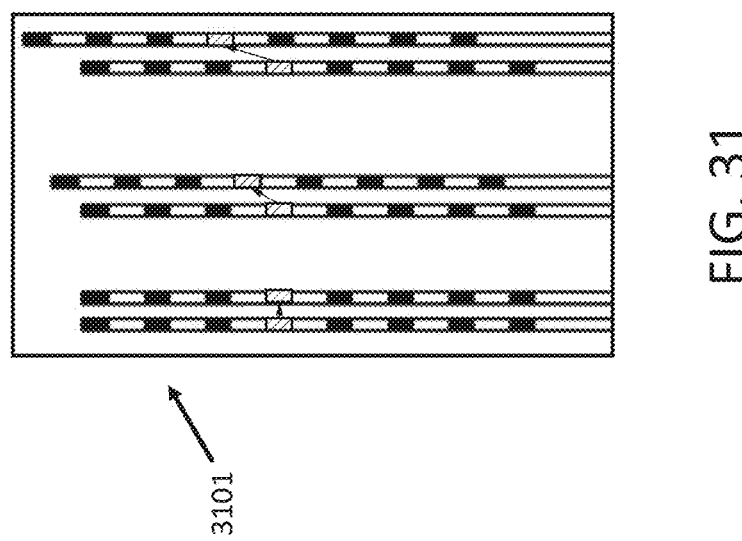
FIG. 31 depicts lead arrangements where the ECAP is generated by the activation of the dorsal column axons and the axonal activation is maximized when the electric field is aligned in the axonal direction according to some embodiments.

In other embodiments of multiple implanted leads, at least one electrode contract from each lead is used to generate ECAPs. The ECAP is generated by the activation of the dorsal column axons and the axonal activation is maximized when the electric field is aligned in the axonal direction (as shown in lead arrangements 3101 of FIG. 31). With lead migration, the angle between the electric field and the axonal direction changes, which results in the percentage of the activated axonal population and the ECAP signal amplitude and morphology. Different stimulation amplitudes, configuration and recording configuration are used and the morphology profile of ECAβ characteristics including the peak to peak value the shape of ECAPs and the latency is assessed. Different configuration of differential recording can be also used. With migration the morphology of ECAP including the peak to peak value shape and latency will be also affected. Combinations of different stimulation electrode pairs and differential recording pairs are tried, and the profiles of ECAβ signals are recorded (which migration the ECAP profiles would alter). In addition to the change of the angle between the electric field and the axonal direction, the change of the surrounding structure of the stimulation and the recording lead will affect the profile of the ECAPs with lead migration. The ECAP threshold amplitude would change when the stimulation electrode contacts are under bony vertebrae compared to inter-vertebral space. In addition to the change of the angle between the electric field and the axonal direction, the change of the distance between anode and cathode will affect the electric field strength resulting in ECAP profile changes.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. A method of providing a neurostimulation therapy to a patient using an implantable pulse generator (IPG), comprising:
    generating electrical pulses by the IPG;
    applying the generated electrical pulses to neural tissue of the patient using one or more electrodes of one or more stimulation leads;
    measuring neural response to the applied electrical pulses through one or more electrodes of one or more stimulation leads using sensing circuitry of the IPG; and
    processing the measured neural response according to wavelet analysis to isolate evoked compound action potential (ECAP) features in the neural response, wherein the wavelet analysis comprises,
        converting the measured neural response from a time domain into a temporal-frequency domain,
        extracting temporal and frequency-based features to conduct signal denoising,
        reconstructing a time-domain signal representing ECAP features.

2. The method of claim 1 further comprising:
    displaying a graph of ECAP features to a clinician on a display of a clinician programmer device.

3. The method of claim 1 further comprising:
    processing data representative of the ECAP features to detect a change in posture by the patient based on one or more ECAP features.

4. The method of claim 3 further comprising:

automatically modifying at least one stimulation parameter for patient therapy in response to detecting a change in posture by the patient.

5. The method of claim 4 further comprising:

stimulation parameter comprising modifying a stimulation amplitude to maintain stimulation by the IPG below a level that generates paresthesia in the patient.

6. The method of claim 1 further comprising:

detecting a change in relative position of a first electrode of a first stimulation lead to position of a second electrode of a second stimulation lead by processing data representative of the ECAP features.

7. The method of claim 1 wherein the processing the measured neural response comprises:

isolating discrete phases of ECAP features in the neural response.

8. The method of claim 1 further comprising:

detecting a shape of ECAP features that differs from an expected shape to detect an undesired patient response to application of the generated electrical pulses.

9. The method of claim 8 further comprising:

detecting muscle activation in response to the application of the generated electrical pulses according to the shape of the ECAP features.

10. The method of claim 1 further comprising:

after isolating ECAP features in a frequency and time domain representation, transforming data indicative of the ECAP features into a one-dimensional time domain to form a reconstructed signal of ECAP values.

11. A neurostimulation system for providing a neurostimulation therapy to a patient, comprising:

an implantable pulse generator (IPG) for generating electrical pulses, wherein the IPG comprises sensing circuitry for sensing neural activity of the patient in response to electrical pulses;

one or more stimulation leads with multiple electrodes for applying electrical pulses to neural tissue of the patient; and an external device adapted to wirelessly communicate with the IPG when the IPG is implanted in the patient, wherein the IPG is adapted to communicated data to the external device indicative of neural activity of the patient in response to one or more electrical pulses; and wherein the external device is adapted to process the measured neural response according to a wavelet analysis to isolate evoked compound action potential (ECAP) features in the neural activity in response to one or more electrical pulses, wherein the wavelet analysis comprises, converting the measured neural response from a time domain into a temporal-frequency domain, extracting temporal and frequency-based features to conduct signal denoising, reconstructing a time-domain signal representing ECAP features.

12. The neurostimulation system of claim 11 wherein the external device is adapted to provide a display of ECAP features to a user of the external device.

13. The neurostimulation system of claim 11 wherein the external device is adapted to detect a change in posture by the patient based on one or more ECAP features.

14. The neurostimulation system of claim 13 wherein the external device is adapted to automatically modify at least one stimulation parameter for patient therapy in response to detecting a change in posture by the patient by communicating one or more control signals to the IPG.

15. The neurostimulation system of claim 14 wherein modification of the at least one stimulation parameter maintains stimulation of the patient by the IPG below a level that generates paresthesia in the patient.

16. The neurostimulation system of claim 11 wherein the external device is adapted to detect a change in relative position of a first electrode of a first stimulation lead to position of a second electrode of a second stimulation lead by processing data representative of the ECAP features.

17. The neurostimulation system of claim 11 wherein the external device is adapted to isolate discrete phases of ECAP features.

18. The neurostimulation system of claim 11 wherein the external device is adapted to detect a shape of the neural response that differs from an expected shape to detect an undesired patient response to application of the generated electrical pulses.

19. The neurostimulation system of claim 11 wherein the external device is adapted to, after isolating ECAP features in a frequency and time domain representation, transform data indicative of the ECAP features into a one-dimensional time domain to form a reconstructed signal of ECAP values.

20. The neurostimulation system of claim 11 wherein the IPG is adapted to provided burst stimulation to the patient for neurostimulation therapy and to provide pinging pulses between therapeutic pulses of the burst stimulation to sense of responsive neural activity of the patient.

* * * * *